(12) United States Patent
Pham

(10) Patent No.: US 11,625,937 B2
(45) Date of Patent: Apr. 11, 2023

(54) METHODS AND SYSTEMS FOR MONITORING HUMAN BODY WEIGHT WITH VEHICLE SENSORS AND BIG DATA AI ANALYTICS

(71) Applicant: TOYOTA MOTOR ENGINEERING & MANUFACTURING NORTH AMERICA, INC., Plano, TX (US)

(72) Inventor: Alexander T. Pham, San Jose, CA (US)

(73) Assignee: TOYOTA MOTOR ENGINEERING & MANUFACTURING NORTH AMERICA, INC., Plano, TX (US)

(*) Notice: Subject to any disclaimer, the term of this patent is extended or adjusted under 35 U.S.C. 154(b) by 340 days.

(21) Appl. No.: 16/840,571

(22) Filed: Apr. 6, 2020

(65) Prior Publication Data
US 2021/0312169 A1 Oct. 7, 2021

(51) Int. Cl.
*G06V 40/10* (2022.01)
*B60N 2/00* (2006.01)
(Continued)

(52) U.S. Cl.
CPC ............ *G06V 40/10* (2022.01); *B60N 2/002* (2013.01); *B60R 11/04* (2013.01); *B60W 40/08* (2013.01);
(Continued)

(58) Field of Classification Search
CPC ........ G06V 20/59; G06V 20/56; B60R 25/10; A61B 5/742; A61B 5/441; H04L 9/30;
(Continued)

(56) References Cited

U.S. PATENT DOCUMENTS 6,793,242 B2 9/2004 Breed et al.
9,173,576 B2 * 11/2015 Yuen .................. A61B 5/742
(Continued)

FOREIGN PATENT DOCUMENTS

CN 106289288 B * 2/2020 ......... G01C 21/3484
WO WO 2018/009219 A1 1/2018

OTHER PUBLICATIONS

Stephanie F. Yeager, et al., "Self-Monitoring—The Way to Successful Weight Management", Obesity Action Coalition (OAC), 2009, 3 pages.
(Continued)

*Primary Examiner* — Yuri Kan
(74) *Attorney, Agent, or Firm* — Oblon, McClelland, Maier & Neustadt, L.L.P.

(57) ABSTRACT

A weight management system for managing vehicle seat occupant body weight by using vehicle cameras and weight sensors of a plurality of vehicles having onboard communication modules. Each vehicle is equipped to analyze and compare weight changes of the vehicle seat occupant over time. Based on the weight status, a weight management recommendation can be transmitted to the vehicle seat occupant. Each vehicle is operatively connected to a weight management application in a data center. The weight management application includes a registration module which registers each vehicle. Additionally, a vehicle seat occupant may register with the weight management application to have his/her weight analyzed when travelling in any of the plurality of vehicles. The weight management application requests a search of a data lake and analysis of search results by a weight data artificial intelligence analytics program to improve the weight management recommendation.

21 Claims, 13 Drawing Sheets

(51) Int. Cl.

| | | |
|---|---|---|
| *G16H 20/60* | (2018.01) | |
| *G06F 16/2458* | (2019.01) | |
| *B60W 40/08* | (2012.01) | |
| *B60W 50/00* | (2006.01) | |
| *G01G 19/44* | (2006.01) | |
| *B60R 11/04* | (2006.01) | |
| *H04L 9/08* | (2006.01) | |
| *G06V 20/56* | (2022.01) | |
| *G06V 20/59* | (2022.01) | |
| *G06V 40/70* | (2022.01) | |
| *B60R 11/00* | (2006.01) | |

(52) U.S. Cl.
CPC ............ *B60W 50/00* (2013.01); *G01G 19/44* (2013.01); *G06F 16/2477* (2019.01); *G06V 20/56* (2022.01); *G06V 20/59* (2022.01); *G06V 40/70* (2022.01); *G16H 20/60* (2018.01); *H04L 9/0825* (2013.01); *B60R 2011/0003* (2013.01); *B60R 2011/004* (2013.01); *B60R 2300/102* (2013.01); *B60R 2300/105* (2013.01); *B60R 2300/8006* (2013.01); *B60W 2050/0075* (2013.01); *B60W 2540/221* (2020.02); *B60W 2556/50* (2020.02)

(58) Field of Classification Search
CPC ............ H04L 9/3297; G01C 21/3415; G01C 21/3641; B60N 2/42736; B60N 2/0246; A23L 33/10; G16H 20/10; G16H 20/60; A61K 38/179; A61K 31/355; G05D 1/0088; G06K 9/00; G06T 13/40
See application file for complete search history.

(56) References Cited

U.S. PATENT DOCUMENTS

| | | | | |
|---|---|---|---|---|
| 9,235,750 | B1* | 1/2016 | Sutton | B60R 25/10 |
| 10,157,423 | B1* | 12/2018 | Fields | G05D 1/0088 |
| 2005/0071197 | A1* | 3/2005 | Goldberg | G16H 20/60 |
| | | | | 600/483 |
| 2009/0149721 | A1 | 6/2009 | Yang et al. | |
| 2018/0042486 | A1 | 2/2018 | Yoshizawa et al. | |
| 2018/0230197 | A1* | 8/2018 | Gouze | A61K 38/179 |
| 2019/0061772 | A1 | 2/2019 | Prinz | |
| 2019/0216366 | A1 | 7/2019 | Hall et al. | |
| 2019/0279069 | A1* | 9/2019 | Bastide | G16H 20/10 |
| 2019/0350997 | A1* | 11/2019 | Tarnopolsky | A23L 33/10 |
| 2020/0164771 | A1* | 5/2020 | Unnervik | B60N 2/42736 |
| 2020/0217677 | A1* | 7/2020 | Wang | G01C 21/3415 |
| 2021/0168602 | A1* | 6/2021 | Kim | H04L 9/30 |
| 2021/0241511 | A1* | 8/2021 | Pai | G06T 13/40 |
| 2021/0334561 | A1* | 10/2021 | Pham | H04L 9/3297 |
| 2021/0338146 | A1* | 11/2021 | Pham | A61B 5/441 |

OTHER PUBLICATIONS

"The pros and cons of weighing yourself every day", American Heart Association News, Jan. 2, 2019, 3 pages.
Adda Bjarnadottir, "Why You May Want to Weigh Yourself Every Day", Healthline Media a Red Ventures Company, https://www.healthline.com/nutrition/daily-weighing, Jan. 3, 2017, 14 pages.
Allison Van Dusen, "Is Your Weight Affecting Your Career?", https://www.forbes.com/2008/05/21/health-weight-career-forbeslife-cx_avd_0521health.html#7f160e84466d, May 21, 2008, 4 pages.
Michele L. Patel, et al., "Comparing Self-Monitoring Strategies for Weight Loss in a Smartphone App: Randomized Controlled Trial", JMIR Mhealth and Uhealth, vol. 7, No. 2, Feb. 28, 2019, 18 pages.
Shigeki Tomoyama, "Toyota's Connected Strategy Briefing", Toyota Motor Corporation, Nov. 1, 2016, 28 pages.

* cited by examiner

METHODS AND SYSTEMS FOR MONITORING HUMAN BODY WEIGHT WITH VEHICLE SENSORS AND BIG DATA AI ANALYTICS

BACKGROUND

Technical Field

The present disclosure is directed to managing the body weight of a vehicle occupant by leveraging vehicle sensors data with weight data stored in a data lake. Weight treatment recommendations are provided to the vehicle occupant.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

As life expectancy rises, body weight and mass index have received growing interest. Large monetary sums are spent each year on weight loss management.

Excess weight has been shown to affect the earning capacity, health, mobility and self-esteem of a person being. In the United States, an estimated 24% of men and 38% of women are trying to lose weight. Meanwhile, obesity has skyrocketed and working-age adults are gaining about 2.2 pounds (1 kg) annually, on average.

In some professions, having a healthy weight may be a positive factor in earning capacity. It has been determined that obesity may lower a woman's annual earnings by as much as 6.2% and a man's by as much as 2.3%. Further, obesity is related to health. It has been estimated that obese employees cost U.S. private companies an estimated $45 billion annually in medical expenditures and work loss. Between 1997 and 2004, obese workers filed twice the number of workers' compensation claims, had seven times the medical costs and lost 13 times the days of work from work injury or illness compared with other employees. Additionally, the average medical claims costs per 100 employees amounted to $51,019 for the obese, compared with $7,503 for the non-obese. By Allison Van Dusen, "Is Your Weight Affecting Your Career?", May 21, 2008, Forbes Media, https://www.forbes.com/2008/05/21/health-weight-career-forbeslife-cx_avd_0521health.html#7f160e84466d, incorporated herein by reference in its entirety).

One behavioral interventional strategy for weight management is self-monitoring of weight. Recent studies have shown that daily weighing may be a powerful tool for both losing and maintaining weight. These studies have found that daily weighing is associated with greater weight loss and less weight gain than less frequent weighing. It was shown that study participants who weighed themselves daily for six months lost an average of 13 pounds (6 kg) more than those who weighed themselves less frequently. Further, those who weighed themselves daily tended to adopt more favorable weight control behaviors, exercised better restraint toward food and developed less impulsive eating habits.

In addition, another study showed that people who weighed themselves every day ate 347 fewer calories per day than those who did not. After six months, the group that weighed themselves daily ended up losing ten times more weight than the control group.

Further, there is a significant link between weighing frequency and weight change. In normal weight individuals, daily weighing resulted in a slight weight loss, while those who weighed themselves monthly gained 4.4 pounds (2 kg), on average. In overweight individuals, those who weighed themselves daily lost 10 pounds (4.4 kg), while those who weighed themselves monthly gained 2.2 pounds (1 kg), on average. Further, it has been shown that frequent weighing is a significant predictor of body weight over time. Participants lost an extra pound (0.45 kg) of body weight for every 11 days they weighed themselves. It is believed that consistent weighing allows a person to catch weight gain before it escalates and to make dietary changes to prevent more weight gain (See: Bjarnadottir, A., "Why You May Want to Weigh Yourself Every Day", Jan. 3, 2017, Healthline, https://www.healthline.com/nutrition/daily-weighing, incorporated herein by reference in its entirety).

Another study, presented at a Scientific Sessions conference of the American Heart Association, also concluded that daily weigh-ins might be beneficial. Researchers tracked 1,042 adults over a year and found that people who weighed themselves once a week or less did not lose weight, while people who weighed themselves six or seven times a week averaged a 1.7 percent weight loss. (See "The pros and cons of weighing yourself every day", Jan. 2, 2019, American Heart Association News, 7272 Greenville Ave. Dallas, Tex., USA, incorporated herein by reference in its entirety).

Many research studies have shown that logging food consumption is instrumental in achieving weight loss. There are many weight loss computer applications which require a person to enter daily food consumption, which aids in calorie management. However, a person may find it time consuming to enter every item of food eaten. (See: Patel, M., "Comparing Self-Monitoring Strategies for Weight Loss in a Smartphone App: Randomized Controlled Trial", JMIR Publications, Vol. 7, No. 2, February 2019, https://mhealth.jmir.org/2019/2/e12209/, incorporated herein by reference in its entirety).

Accordingly, it is one object of the present disclosure to provide methods and systems for managing the weight of a vehicle occupant. An external vehicle camera performs a body scan prior to or when the vehicle occupant enters the vehicle. Weight sensors record the weight of the vehicle occupant each time he/she occupies a seat in the vehicle. Weight changes over time may be correlated to trip information related to food consumption, such as stops at restaurants. The vehicle occupant's weight, body scan and trip information may be transmitted to a computer application in a data center with access to a data lake and weight data artificial intelligence (AI) analytics. Based on the weight data search results, recommendations for weight management may be made.

SUMMARY

In the exemplary embodiments, methods, systems and non-transitory computer readable medium having instructions stored therein that, when executed by one or more processor, cause the one or more processors to perform a for managing the weight of a vehicle seat occupant using vehicle cameras and vehicle weight sensors, comprising detecting an approach of the vehicle seat occupant to the vehicle and generating a presence signal, performing a body scan of the vehicle seat occupant upon receiving the presence signal, timestamping and storing the body scan in a vehicle memory, determining a set of body scan parameters from the body scan of the vehicle seat occupant, recording a sensor signature of the vehicle seat occupant, identifying the vehicle seat occupant by matching the sensor signature to a set sensor signatures of registered vehicle seat occupants stored in the vehicle memory, measuring a current body weight of the vehicle seat occupant, timestamping and storing the current body weight in the vehicle memory, determining changes between the current body weight and at least one stored body weight of the vehicle seat occupant having a timestamp recorded during an earlier time period, accessing GPS records regarding venues visited by the vehicle seat occupant during the earlier time period, correlating the weight changes, the set of body scan parameters and the GPS records of venues visited with weight information stored in the vehicle memory to generate a weight analysis, generating a weight management recommendation from the weight analysis, notifying the vehicle seat occupant of the weight management recommendation, updating the vehicle memory with the weight management recommendation, and transmitting the body weight changes and the body scan parameters to a data lake.

In an embodiment, the weight management recommendation is generated solely by a CPU of the vehicle.

In a further embodiment, an initial weight analysis is performed by the CPU to determine a weight changes and body scan parameters and a weight management application is accessed to search a data lake for related weight information. The weight information is analyzed using weight data artificial intelligence analytics to improve the weight management recommendation.

In another embodiment, the method includes combining the vehicle seat occupant identification, the body weight changes, the set of body scan parameters and the GPS records of venues visited into a data packet and transmitting the data packet to the weight management application. The weight management application requests a search related to the vehicle seat occupant body weight changes, the set of body scan parameters and the GPS records of venues visited. The method continues by receiving the request by a weight data artificial intelligence (AI) analytics module, querying the data lake for information relating to the vehicle seat occupant body weight changes, the set of body scan parameters and the GPS records of venues visited, searching, by the data lake, unstructured data and structured databases for matches to the query, receiving, by the hair and scalp data AI analytics module, the matches to the query, analyzing, by the weight data AI analytics module, the matches to determine weight conditions, treatment options for the weight conditions and at least one of weight loss or weight gain product information related to the weight conditions, generating, by the weight data AI analytics module, a weight report, providing the weight report to the weight management application for correlation with the vehicle seat occupant user profile, generating a weight management recommendation, transmitting the weight management recommendation to the vehicle, updating the vehicle memory, and delivering the weight management recommendation to the vehicle seat occupant.

In yet another embodiment, the vehicle seat occupant registers a smart device with the weight management application stored in a data center. When the vehicle seat occupant enters any one of a plurality of vehicles registered with the weight management application, the vehicle is instructed to perform a body scan and record the vehicle seat occupant's body weight and to transmit the body scan and body weight to the weight management application. The weight management application performs the tasks of analyzing the weight changes and the body scan and requests a search of the data lake. A weight data AI analytics module creates search queries based on the body weight changes, the body scan parameters and the GPS trip records and forwards the search queries to the data lake. The data lake searches unstructured data and structured data and returns the search results to the weight data AI analytics module. The weight data AI analytics module analyzes the search results and provides the analysis to the weight management application. The weight management application correlates the analysis with the user profile of the vehicle seat occupant and generates a weight management recommendation, which is transmitted to the smart device.

In an additional embodiment, body weight changes, the body scan parameters and anonymized user profile information from a plurality of vehicle seat occupants of a plurality of vehicles are stored in the data lake.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
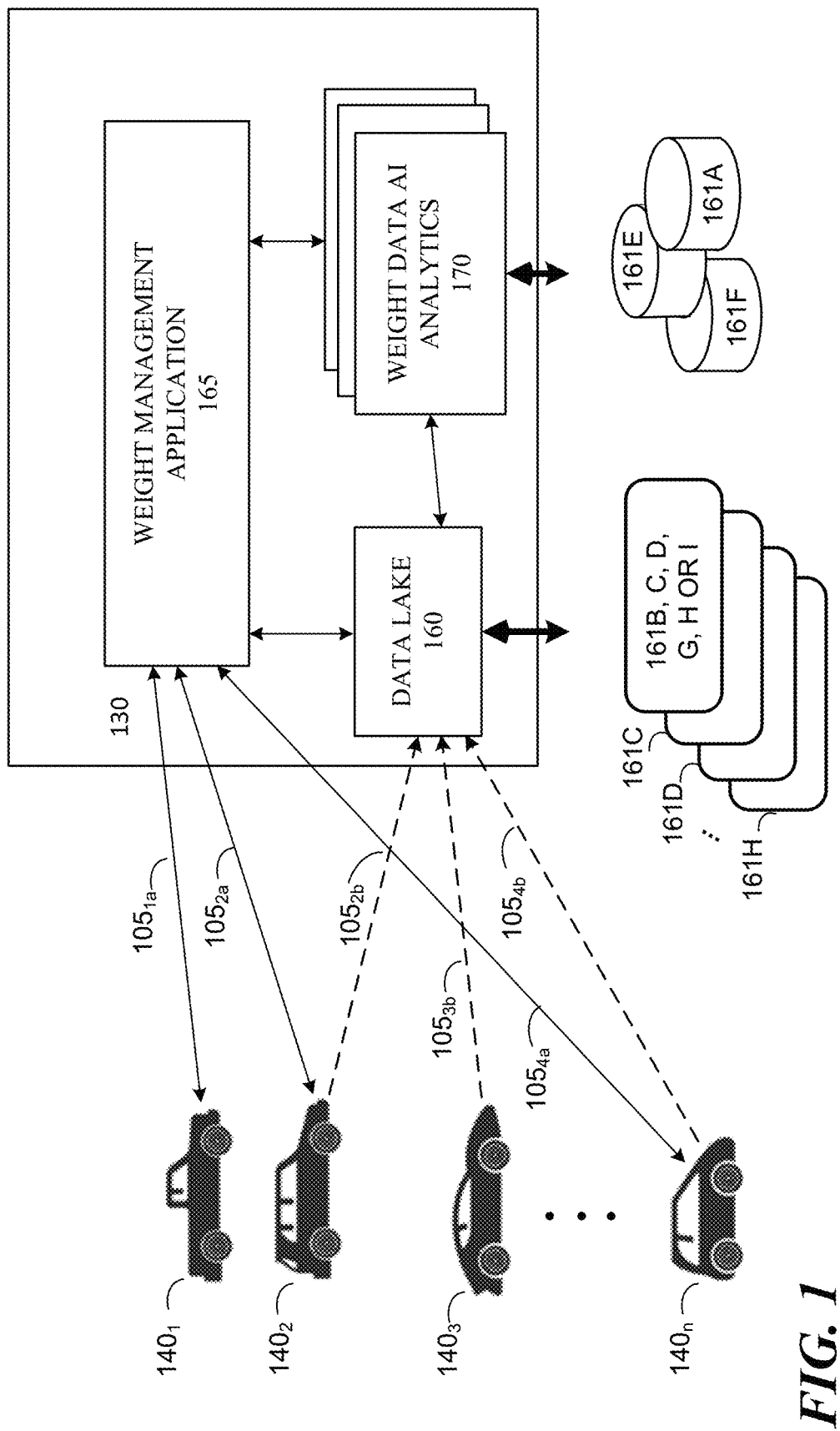
FIG. 1 is an illustration of the weight management system, according to certain embodiments.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values therebetween.

"Big data" includes information garnered from social media, data from internet-enabled devices (including smart phones and tablets), machine data, video and voice recordings, and the continued preservation and logging of structured and unstructured data. Big data refers to the dynamic, large and disparate volumes of data created by people, tools and machines which are distributed over a set of storages. The data gathered may be stored beforehand or may be a continuous stream to be accessed, stored and analyzed with distributed algorithms and frameworks.

"Big data artificial intelligence (AI) analytics" is the often complex process of examining large and varied data sets, or weight data, to uncover information, such as hidden patterns, unknown correlations, market trends and customer preferences that can help users make informed decisions. Big data analytics requires a set of distributed computing, networking and storage resources that may be available locally or are rented from a cloud infrastructure or data center. In this manner, weight data is related to cloud computing.

The Toyota Big Data Center collects and analyzes data from vehicles equipped with a Data Communication Module (DCM), using a next-generation connected-vehicle framework, which transmits data over cellular networks. The Toyota Big Data Center (TBDC) in the Toyota Smart Center analyzes and processes data collected by the DCM, and uses the data to deploy services under high-level information security and privacy controls. (See "Toyota Accelerates Its Connected Car Technology Initiatives", 2016, https://pressroom.toyota.com/releases/toyota+connected+car+technology+accelerates.htm, and "Toyota's Connected Strategy Briefing", 2016; "Toyota to make "Connected Vehicles" its new standard in Japan, Jun. 26, 2018, https://global.toyota/en/newsroom/corporate/23157821.html, each incorporated herein by reference in its entirety).

A "data lake" is a storage mechanism designed to facilitate the colocation and use of many different types of data, including data that is date-defined using various schemata, structural frameworks, blobs and other files. A data lake is a system or repository of data stored in its natural/raw format, usually object blobs or files. A data lake may contain a single store of all enterprise data including raw copies of source system data and transformed data used for tasks such as reporting, visualization, advanced analytics and machine learning. A data lake can also include structured data from relational databases (rows and columns), semi-structured data (CSV, logs, XML, JSON), unstructured data (emails, documents, PDFs) and binary data (images, audio, video). A data lake is a centralized repository which stores structured and unstructured data at any scale. The data may be stored as-is, without having to first structure the data. Different types of analytics, from dashboards and visualizations to weight data processing, real-time analytics, and machine learning operate on the data from the data lake to guide better decisions.

A "data warehouse" is a database optimized to analyze relational data coming from transactional systems and line of business applications. The data structure, and schema are defined in advance to optimize for fast SQL queries, where the results are typically used for operational reporting and analysis. Data is cleaned, enriched, and transformed so it can act as the "single source of truth" that users can trust.

A data lake is different from a structured data warehouse, as it stores relational data from line of business applications, and non-relational data from mobile apps, IoT devices, and social media. The structure of the data or schema is not defined when data is captured. This means the data can be stored without careful design or the need to know its future purpose. Different types of analytics this data like SQL queries, weight data analytics, full text search, real-time analytics, and machine learning can be used to uncover insights. The data lake of the present disclosure may contain unstructured data sourced from a plurality of connected vehicles, and may not necessarily contain only weight data. For example, the data lake may contain information related to vehicle operating parameters, images of the surrounding environment which may be used in mapping or GPS route determination, speed of the vehicle or surrounding vehicles, etc.

"Cloud computing" is network-based computing in which typically large collections of servers housed in "data centers" or "server farms" provide computational resources and data storage as needed to remote end users. Some cloud computing services provide access to software applications such as word processors and other commonly used applications to end users who interface with the applications through web browsers or other client-side software. In the present disclosure, the weight management application may be stored in a data center or may be stored in a separate server system, such as an application server stored in a cloud network, which is connected to the data center.

The weight management software application is deployed in the data center. The data center includes access to storage systems, databases, analytics programs, as needed, that can provide functionality that is required by the application.

Aspects of this disclosure are directed to a method for managing the weight of a vehicle seat occupant using vehicle cameras and vehicle sensors, a system for managing the weight of a vehicle seat occupant and non-transitory computer readable medium having instructions stored therein that, when executed by one or more processors, causes the one or more processors to perform a method for managing the weight of a vehicle seat occupant using vehicle cameras and vehicle sensors. Aspects of the present disclosure describe generating weight management recommendations by utilizing weight data artificial intelligence analytics and data from a data lake.

An overview of the system for managing weight is shown in FIG. 1. Vehicles $140_1$, $140_2$, $140_3$, $140_n$ each include an onboard communication system which is configured to communicate with data center 130. A weight management application 165 is stored on a data center 130 and may access the data lake 160 and weight data artificial intelligence (AI) analytics program 170 in performing the weight management. Weight data AI analytics 170 may be used to generate search queries which are transmitted to the data lake 160. The data lake 160 may use the search queries to search unstructured (raw) data and a plurality of structured databases (161A, 161E, 161F) and data warehouses (161B, C, D, G, H or I), such as medical databases, fitness applications, weight and fitness journals, hospital records, research articles, weight loss or weight gain product information, and the like, as shown in FIG. 3B. The data lake 160 may store the search results with weight records of seat occupants of each of the vehicles 140, along with weight management recommendations and anonymized user profile information, such as age, height, ethnic group, income group, and the like, for use in future weight analyses. Additionally, every vehicle connected to the weight management application uploads its raw weight data to the data lake periodically over communication paths 105$_2$ (105$_{2a}$, 105$_{2b}$, etc.) The upload of raw data to the data lake may be performed when a vehicle is parked in a garage with Wi-Fi or data connectivity and is not necessarily uploaded continuously.

The data center 130 may be connected to the onboard communication module 210 through a network. The network can be a public network, such as the Internet, or a private network such as a local area network (LAN) or a wide area network (WAN) network, or any combination thereof and can also include a public switched telephone network (PSTN) or integrated services for digital network (ISDN) sub-networks. The network may wireless such as a cellular network including EDGE, 3G, 4G, and LTE/LTE-A wireless cellular systems. The wireless network can also be Wi-Fi, Bluetooth, or any other wireless form of communication that as is conventionally known.

The internal and external sensors(s) of a vehicle can be configured to record the weight of a vehicle occupant at regular intervals (such as several times per day, over weeks, months and years or every time the person enters the vehicle). Comparisons of these weight records may be able to provide weight analyses useful in weight management, since the weight records may represent a long and extensive history of the weights of the driver and passengers. The time period of comparison is preferably in the range of one hour to five years, more preferably in the range of one hour to one year, most preferably in the range of one hour to two months. In a non-limiting example, current weight data may be compared with weight data stored at one week intervals for a period of 6 months, to generate a weight loss or gain report which spans 6 months. This report may be included in the weight management recommendation.

Big data collected by vehicle sensors can include millions and possibly billions of weight records of people of all ages, genders, ethnic groups, body types, etc. Medical and other data related to weight management and information on recommended treatment may be stored in the data lake. Based on this data, the weight management application can correlate the weight images with the medical data and other data and determine a weight management recommendation. The weight management application further can store a medical database of physicians, lists of fitness centers and fitness regimes, weight loss professionals, and the like, and may recommend a physician, fitness center, fitness regime or weight loss professional near the home or current location of the driver or passenger. The weight management application can also store information related to weight loss or weight gain products and may recommend products which aid in weight management.

In an aspect of the present disclosure, the weight management application may be installed on the vehicle and work as a standalone system. The vehicle memory may hold statistical groupings which can be matched to weight changes as detected by the vehicle cameras and weight sensors. The processing of the weight changes and analysis may be performed solely by the vehicle computing system. When the vehicle is in an area which allows for data communications, the vehicle may sync with the weight management application to report the weight changes and its analysis.

In an aspect of the present disclosure, the weight management application may be a subscription based application and/or may be included with the vehicle. In either case, the identities of the driver and passengers are protected by strict high-level information security and privacy control.

In another aspect, the subscription is registered to the vehicle. In a non-limiting example, the weight management application may offer the weight analysis to an anonymized driver/owner without the need for strict privacy controls.

In a further aspect, the vehicle may register with the weight management application. In this aspect, the vehicle performs a body scan, weighs and identifies the vehicle seat occupant and detects changes in weight between a current weight and an earlier, stored weight record of the vehicle seat occupant. The vehicle transmits the weight changes and identity of the vehicle seat occupant to the weight management application for further processing and search of a data lake. A weight management recommendation is generated by the weight management application and delivered to the vehicle seat occupant through the onboard communication system of the vehicle. In another aspect, a vehicle seat occupant may register with the weight management application and user profile information may be sourced from his/her smart device and/or social media contacts. When the vehicle seat occupant is seated in a vehicle registered with the weight management application, the weight management application requests that the vehicle perform body scan and weight recording. In this aspect, the vehicle seat occupant may not have travelled in this vehicle before, therefore the body scan and weight recording are sent to the weight management application. The weight management application maintains a larger database for storing the weight records of the vehicle seat occupant and amasses weight records every time he/she enters a registered vehicle. In this aspect, the comparison of the weight records is performed by the weight management application.

In every aspect mentioned above, the weight records are sent to the data lake to become part of the raw data. Certain user profile statistics may accompany the weight records, such as age, height, BMI, ethnic group, income group, educational level, medical conditions. The weight records are otherwise anonymized before transmission to the data lake.

Figure 2A:
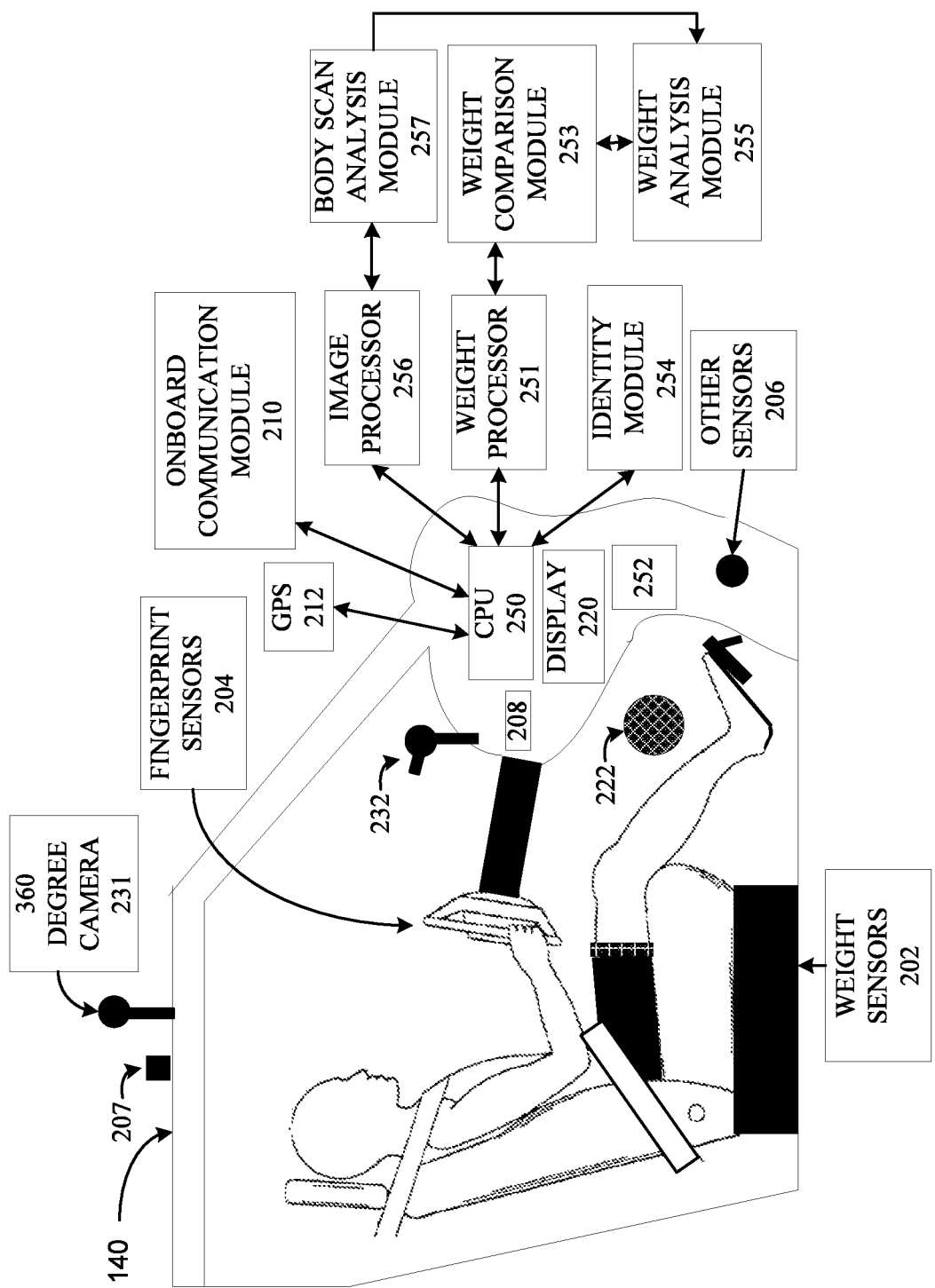
FIG. 2A illustrates a vehicle having an onboard communication module and weight analysis capability, according to certain embodiments.
Figure 2B:
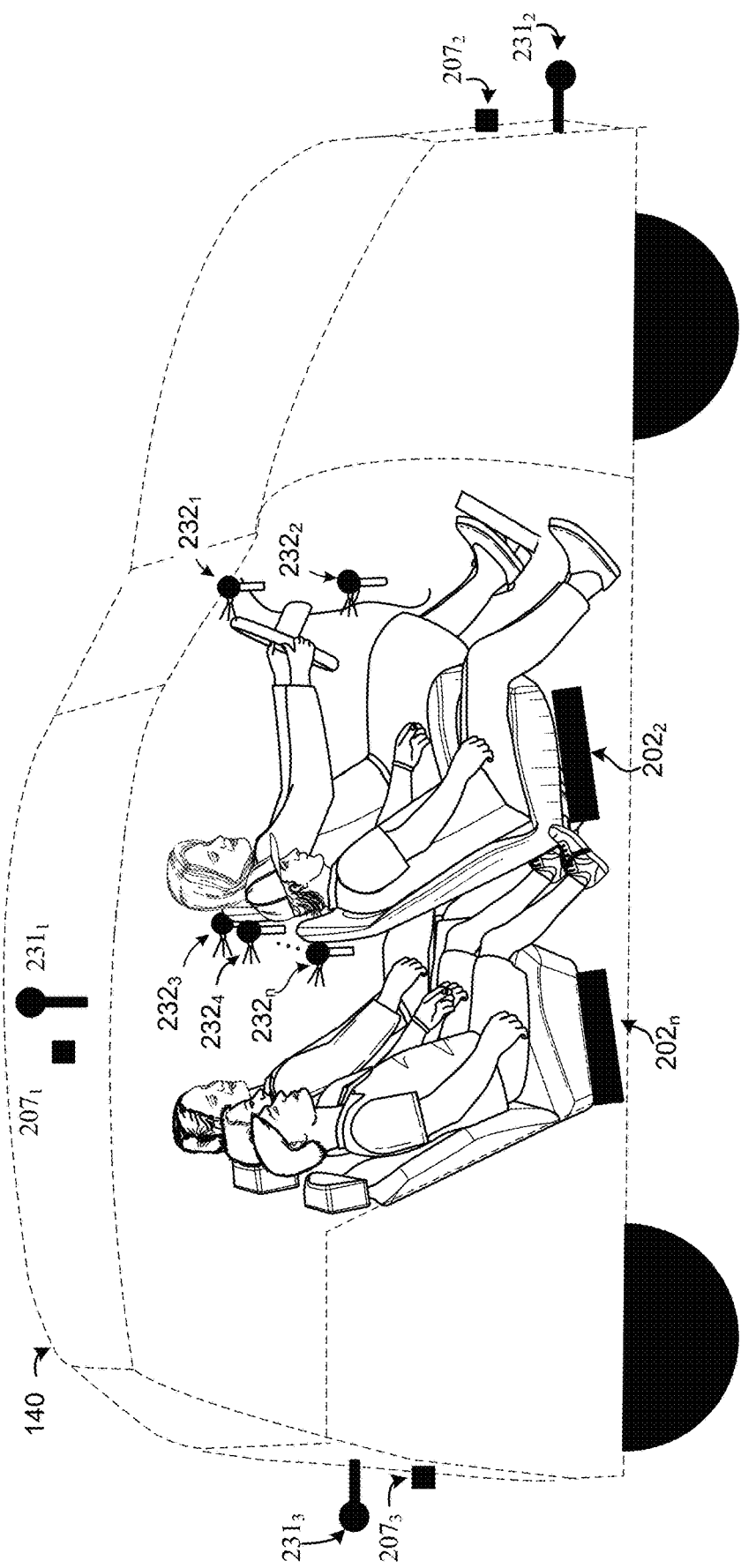
FIG. 2B illustrates cameras and weight sensors arranged to identify vehicle seat occupants, according to certain embodiments.

In order to determine the weight of a vehicle seat occupant, a body scan may be performed as the potential vehicle seat occupant approaches a vehicle 140. Referring to FIGS. 2A and 2B, the vehicle may have a plurality (M) of exterior 360 degree cameras, 231$_1$, . . . , 231$m$. These cameras may have "fish-eye" lenses, which can capture a large field of view. Alternatively, the cameras may be configured with motion detection and mobility capability, such that they turn in the direction of a person who approaches the vehicle. Camera images from the plurality of cameras may be stitched together to form a composite image by image processor 256.

A body scan analysis module 257 receives the body scan from image processor 256. The body scan analysis module 257 determines sets of body scan parameters, such as apparent weight, height, BMI, waist thickness, and other body dimensions. The body scan analysis module may compare the sets of body scan parameters with sets of body scan parameters stored in memory 252. Memory 252 may include a database of previous weights and sets of body scan parameters along with identification of the vehicle occupant, for each occupant of the vehicle.

The body scan may also be used to identify the occupant by comparing the sets of body scan parameters with prior sets of body scan parameters stored in a user profile.

The body scan analysis module 257 may determine that the seat occupant has gained or lost weight. Determination that the seat occupant has gained or lost weight may trigger the weight analysis module 255 to begin analyzing the causes of the weight change.

Whether subscription based or a standalone vehicle program, the driver and passengers of the vehicle may be identified (in identity module 254) by the body scan, in-vehicle cameras or by other sensors, such as weight sensors 202, retinal readers (other sensors), voice recognition (other sensors 206) or fingerprint readers 204. Fingerprint readers 204 may be located on the steering wheel or may be in another location near the interior dashboard or on a user interface 208. Further, a passenger may be identified by a body scan, in-vehicle camera or by fingerprint readers. The identification of the driver or passengers is not limited to weight sensors, camera images or fingerprint readers. The identification may also be made by any of retinal readers, voice recognition, or the like.

Weight sensors 202 measure the body weight of a vehicle seat occupant each time he/she occupies a seat. A weight processor 251 records the body weight measurement for each seat occupant, timestamps the weight measurement and stores the weight measurements in memory 252. Weight comparison module 253 compares the current weights to weights with earlier timestamps which have been stored in the memory 252, and collected over a time period, for example, over the last three month period. The comparisons are sent to the weight analysis module 255. The weight analysis module also receives the body scan analysis from body scan analysis module 257. The weight analysis module may detect a change in the vehicle seat occupant's weight. Upon determining a weight change, the weight analysis module may search trip information stored in the memory (determined from GPS unit 212). The trip information may be searched for trips to restaurants, fast food restaurants, fitness centers, grocery stores, and the like. The weight analysis module may make a weight management recommendation to the vehicle seat occupant based on correlating the trip information with the weight changes.

In a non-limiting example, the vehicle system may send a notification alert, such as: "You have gained 5 pounds within the past 3 months. You visited at least one of the following fast food restaurants three times per week. Each of these restaurants has food with high caloric value. It is recommended that you visit the following list of lower calorie restaurants." or "You have visited your fitness center every day for the last month. You have lost ten pounds and are now below your goal weight. It is recommended that you decrease your visits to the fitness center to three times per week for the next month."

The weight analysis module 255 may transmit the weight changes, body scan parameters, identity of the vehicle seat occupant and weight analysis, by onboard communication module 210), over communications paths $105_1$ ($105_{1a}$, $105_{1b}$, etc.) to the weight management application (165, 365, FIG. 1, 3A) for search of data lake (160/360).

The weight management application requests a search of the data lake by weight data AI analytics 170. The weight data AI analytics 170 creates search queries related to the weight record which are transmitted to the data lake. In non-limiting examples, the data lake may be searched with search tools, such as Elastic Search, Azure Data Explorer and Talend. The data lake searches within the unstructured and structured data to determine information related to the weight changes.

The data lake may use the search queries to search within its unstructured and structured data and also to search a multitude of weight related warehouses, such as medical databases, weight gain/loss product websites, weight management professionals, dieticians, weight management blogs, weight management articles, fitness management databases, hospital records, and the like. The data lake 160 may store the search results with weight records of seat occupants of each of the vehicles 140, along with weight management recommendations and anonymized user profile information, such as age, height, weight, ethnic group, income group, and the like, for use in future weight analyses.

In a non-limiting example, the data lake may store the names of medical professionals or weight loss centers in the home area of an identified driver or passenger. In a further non-limiting example, the data lake may store the names of medical professionals or weight loss centers in the current location of the connected vehicle 140 based on GPS data received from the vehicle. In another non-limiting example, the data lake may store lists of weight gain/loss products recommended for weight management and provide the names of retail outlets which carry the products and which are in the current or home location of the driver or passenger.

The weight management application may suggest weight loss/gain products, a weight care regime, low calorie foods, vitamin supplements. Additionally, the weight management application may recommend that the driver/passenger visit a weight management professional, and provide a list of professionals in either the current or the home area of the seat occupant. The weight management application may contact a medical professional who may provide feedback regarding the weight change. In a non-limiting example, a vehicle seat occupant may have a weight gain as determined by the weight analysis module 255 or the weight management application 365. The weight management application may report the weight gain to the primary physician of the vehicle seat occupant. The primary physician may respond with a referral to a dietician. The weight management application may add the referral and physician's notes to the weight management recommendation.

The vehicle memory 252 may be updated by the recommendations from the weight management application.

In a further non-limiting example, either the weight analysis module 255 or the weight management application 365 may determine that the weight change is unusually large. The vehicle may further include sensors on the steering wheel which measure the driver's heart rate. Based on the weight change and heart rate, a health score may be determined. An alert may be sent to the driver to pull over and an ambulance may be called by the vehicle system if the health score is dangerously high.

The methods of the present disclosure include levering artificial intelligence (AI) and analytics technology, to provide baselines for each weight type.

Aspects of the present disclosure may use weight data sources to obtain current and historical and/or predictive information to form a weight analysis database.

For example, current and historical information may be sourced from a data lake database compiled from the weights and sets of body scan parameters of other drivers/ passengers of vehicles (140$_1$, 140$_2$, 140$_3$, 140$n$) connected to the weight management application. The data lake database may further include body weight parameters which have been previously correlated to weight management information, such as sourced from medical databases.

As shown in FIG. 2A, vehicle 140 includes a control system including a CPU 250, an onboard communication module 210, a GPS unit 212, a display 220, an image processor 256, a body scan analysis module 257, a weight analysis module 255, a memory 252, one or more cameras 232, one or more 360 degree cameras 231, fingerprint sensors 204, GPS unit 212, a weight processor 251, a weight comparison unit 253, a weight analysis module 255, speakers 222, a display 220 and a user interface 208. Weight sensor(s) 202 beneath or in each seat determine the weight of the seat occupant. Camera 232 may be directed to the face of the driver or toward the face of a passenger to record facial images. The vehicle may have a plurality of cameras (232$_1$-232$_n$, FIG. 2B) directed to driver or passenger locations. These facial images and their timestamps are sent to the CPU 250, which includes circuitry for processing the images by image processor 230, and storing the facial images in memory 252. The CPU 250 may identify the driver or passenger by the facial images via identity module 254 and may store the facial images in a database including a profile image of the driver or passenger. The profile image may be updated by the current image. Additionally, the CPU 250 may be configured to use the facial images with data obtained from the other vehicle sensor(s), such as fingerprint sensors 204 on the steering wheel, the weight sensors 202, other sensors 206, such as audio sensors, heart rate sensors or the like, or inputs at a user interface 208 to determine the identity of the seat occupant of the vehicle.

Referring to FIG. 2B, the vehicle 140 may include the plurality of cameras (232$_1$, 232$_2$, 232$_3$, 232$_k$), wherein a camera is directed at the level of a face of a person seated in each different seat position. Weight sensors (202$_1$, 202$_2$, . . . , 202$_n$) beneath or within each seat may indicate whether the seat is occupied and the weight of the seat occupant, which is sent to weight processor 251. The CPU 250 includes circuitry configured to adjust the focus and direction of the camera lens based on the weight of the occupant, which may indicate the height of the occupant. For example, a weight of 55 pounds may indicate a child of about 7 years. A range of average heights stored in memory 252 can be determined for the weight. Alternatively, the weight and height of each seat occupant may be stored at the time of registration and used to redirect the camera field of view. The height may be adjusted over time by the identify module if the vehicle occupant is a child. Alternatively, the vehicle computing system may identify the seat occupant by the body scan conducted from images taken by 360 degree cameras (231$_1$, 231$_2$, 231$_3$). The number of 360 degree cameras is not limited to three and may be a plurality of cameras focused to take images for the body scans of each seat occupant as he/she enters the vehicle.

In addition, the identity module may request the input of a voice of the seat occupant, a fingerprint may be requested at the user interface 208, or the like, to generate an identification of the seat occupant.

The image processor receives the images and weights of the identified driver or passenger and stores the images and weights in a database in memory 252. Memory and/or database may store user profiles of drivers and passengers of the vehicle, profile images and historical weight parameters of each driver and passenger.

The body scans and weights of each driver or passenger are stored over time, such as days, weeks, months and years. These body scans may compared by body scan analysis module 257 to determine changes in the images over time. The time period of comparison is preferably in the range of one hour to five years, more preferably in the range of one hour to one year, most preferably in the range of one hour to two months. The vehicle includes a weight analysis module 255, which determines a weight change, such as a change in BMI, waist thickness, weight and the like from the body scan and changes in the images. The weight analysis module 255 searches the memory for trip or purchase information which may indicate causes of the weight change.

The weight analysis module may provide audio (on speakers 222) or displayed feedback (on display 220) directly to the identified driver or passenger, such as "You have gained five pounds this month. It is recommended that you cut your caloric input by 500 calories per day to reach your goal weight."

Alternatively, the weight analysis module may recommend medical treatment when rapid weight gain/loss appears to be indicated. If a user profile contains the names and telephone numbers of medical professionals known to the identified driver or passenger, the weight analysis module may ask if the driver or passenger would like to call the medical professional, and the onboard communication module may process the call. Alternatively, the weight analysis module may recommend a medical professional from a stored list of medical professionals in the home location of the identified driver or passenger. In a non-limiting example, the feedback provided may be "Your BMI of 42 and current heart rate measurements indicate that you are at risk from heart attack or stroke. Dr. XXX is a cardiologist in your home area. Do you wish to call Dr. XXX to make an appointment?". The CPU 250 may then dial the call to Dr. XXX.

Figure 3A:
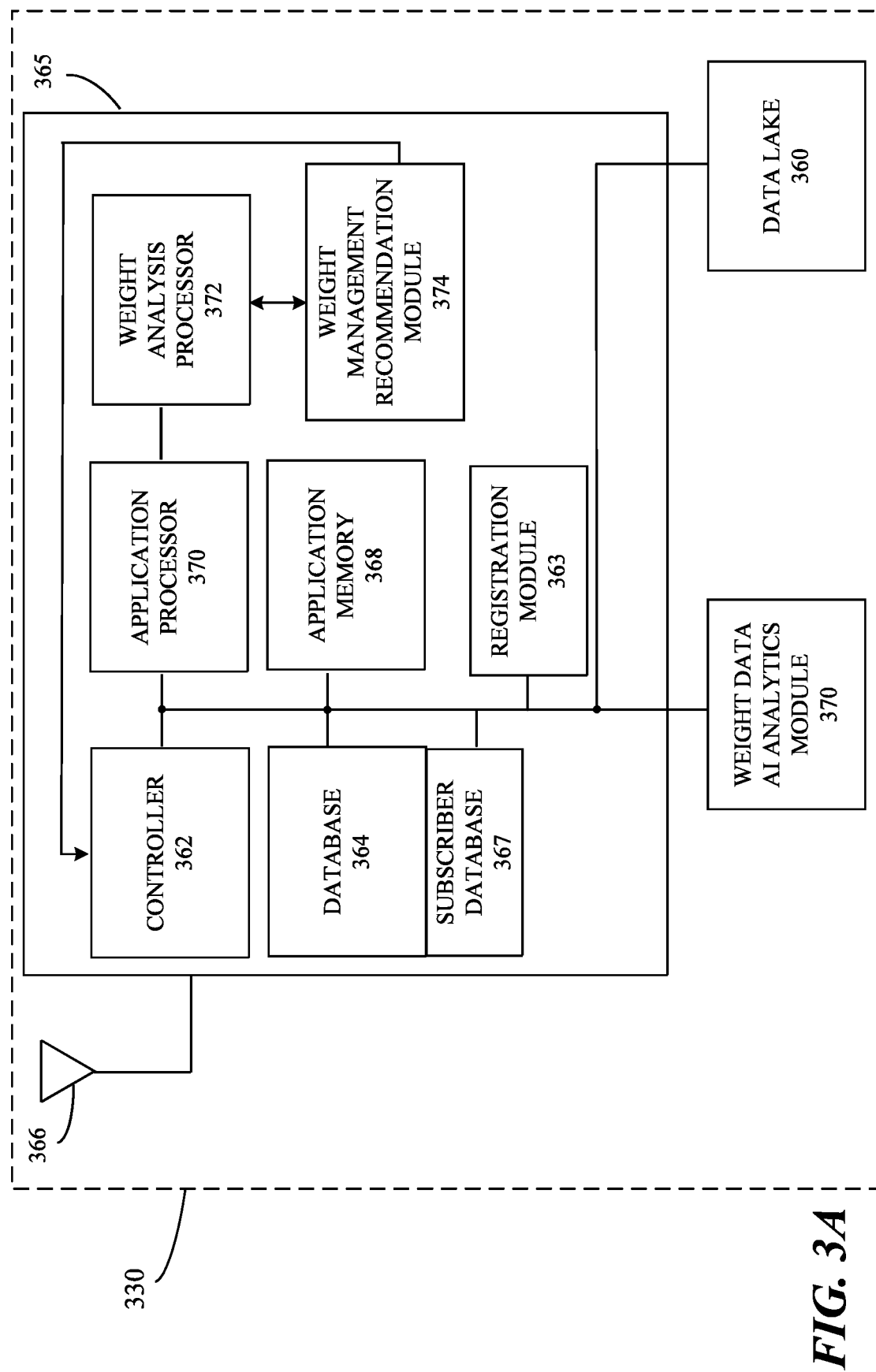
FIG. 3A depicts the computing system of the weight management application, according to certain embodiments.
Figure 3B:
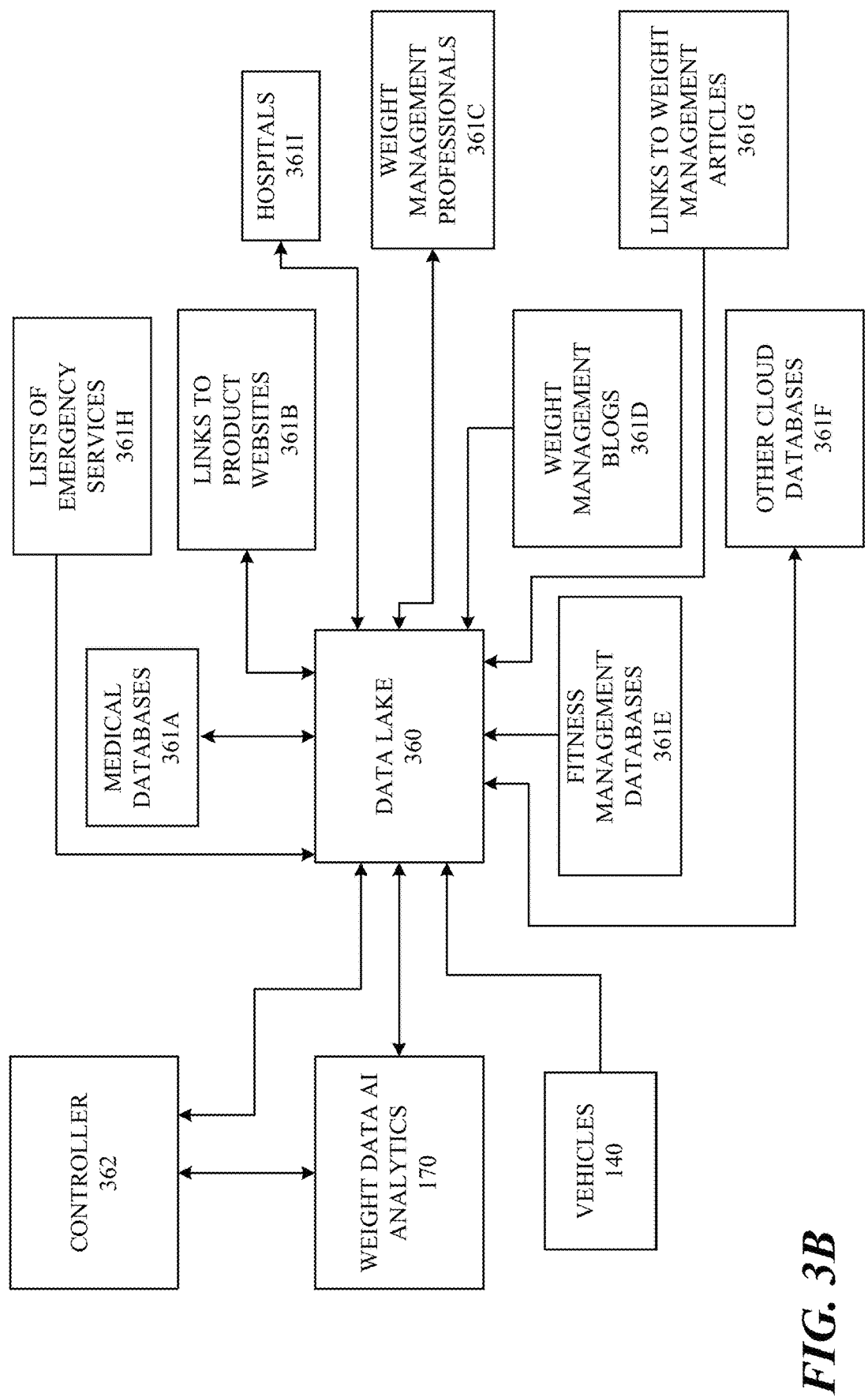
FIG. 3B is a block diagram of the data lake as connected to the vehicles, weight data AI analytics, data warehouses, databases and the weight management application, according to certain embodiments.

The weight analysis module 255 may work in conjunction with weight management application 165, which is able to provide more extensive weight analysis through accessing the data lake 360 and weight trained search and AI analytics program 370 as shown in FIG. 3A. The weight analysis module 255 of the vehicle may be updated by the weight management application 365.

The CPU 250 is implemented, for example, using one or more ECUs. In particular, the CPU 250 is communicatively coupled to the one or more sensors (202, 204, 206), display 220, image processor 256, body scan analysis module 257, weight processor 251, weight comparison module 253, weight analysis module 255, memory 252, and one or more cameras 231 and 232 to receive data therefrom, for example, via a transmission or signal wire, a bus (e.g., a vehicle CAN), radio frequency, etc. Further, the CPU 250 is communicatively coupled to the onboard communication module 210 to transmit and receive communications to or from the weight management application 165 in the data center 130.

The CPU 250 may comprise a single Central Processing Unit (CPU), or could comprise two or more processing units. For example, the processing unit 250 may include general purpose microprocessors, instruction set processors and/or related chips sets and/or special purpose microprocessors such as Application Specific Integrated Circuits (ASICs). The processing unit 250 may also comprise a memory or storage for caching and other purposes. Those of ordinary skill in the art understand that any other node, controller, unit, database and/or device described herein may be similarly implemented.

Principal components of a CPU include an arithmetic logic unit (ALU) that performs arithmetic and logic operations, processor registers that supply operands to the ALU and store the results of ALU operations, and a control unit that orchestrates the fetching (from memory) and execution of instructions by directing the coordinated operations of the ALU, registers and other components.

The memory 252 is a computer readable medium and is connected to the CPU 250. The memory stores computer readable instructions e.g. in the form of computer program modules. For example, the memory 260 may be a flash memory, a Random-Access Memory (RAM), a Read-Only Memory (ROM) or an Electrically Erasable Programmable ROM (EEPROM).

The weight analysis module 255 may access a database in memory 252 when analyzing the weight changes. The weight changes, body scan parameters, GPS trip records and identity of the seat occupant are transmitted in a data packet by onboard communications module 210 to weight management application 165 in data center130 for further analysis. Alternatively, the weight management application may be implemented in any one of a cloud computing environment, a web application residing on one or more servers, a website, a blockchain system and a distributed server system. The weight management application may update the in-vehicle weight analysis module 255 with the recommendations.

Within the data center 130, the weight management application 165 has access to data lake 160 and to weight data (AI) analytics programs 170. Weight data AI analytics uses algorithms to find subtle relationships in a large set of "training" data, such as weight data received from connected vehicles 140 (a vehicle having an onboard communications system which is capable of transmitting and receiving over LTE, 3G, 4G or 5G is known as a "connected vehicle"). The training process locates those relationships and encodes them into a "model," such as a neural network. The model can then be used to find relationships between inputs similar to those in the training data. The trained model itself may reside anywhere it can receive inputs and provide outputs.

As shown in FIG. 3A, the weight management application (165, 365, FIG. 1, 3A) may include a controller 362, at least one database 364 including subscriber data 367, at least one transceiver 366, at least one application memory 368 including program instructions, an application processor 370 operatively connected to weight analysis processor 372, which is configured to use the program instructions to analyze weight data received from the onboard communications module 210 of a connected vehicle 140 and correlate the information with data received from a data lake 360 of similar weight parameters. Weight data AI analytics 370 may be configured to prepare search queries for searching the data lake for the causes and treatments for the weight gain/loss. The data lake 360 stores unstructured (raw) data, such as the body weight changes, body scan parameters and anonymized user profile information. The data lake may further store the information regarding management of the weight gain/loss. In a non-limiting example, the data lake may store the names of medical or weight management professionals in the home area of the identified driver or passenger. In a further non-limiting example, the data lake may store the names of weight management or medical professionals in the current location of the connected vehicle 140 based on GPS data received from the vehicle. In another non-limiting example, the data lake may store lists of weight management products recommended for the weight gain/loss of the identified driver or passenger, and provide names of retail outlets in the current or home location which carry the products.

The database 364 can represent one or more local and/or external databases and/or memory 368 communicably coupled to the controller 362. A subscriber database 367 can store a user profile including historical weight images or weight analyses, physicians, weight management professionals, dieticians, fitness centers, fitness regimes, weight gain/loss products, and preferred retail outlets of the identified driver or passenger.

The data center 130 can represent one or more servers communicably coupled to the onboard communication module 210. For example, the server can include processing circuitry configured to operate the system 100, receive data from the onboard communication module 210, receive statistical information from the database 364 or subscriber database 367, and the like. The server may include an application server which hosts a web application which performs some or all of the processes of the weight analysis service. The server may include a communication endpoint or find other endpoints and communicate with those endpoints. The server may share computing resources, such as CPU and random-access memory over a network. The server may be a virtual server or a web server. The cloud network enables the communication between the on-board communication module, satellites or base stations and the at least connected vehicle 140.

The processing circuitry of the weight management application 365 residing on the server can carry out instructions to perform or cause performance of various functions, operations, steps or processes of the system 100. The controller 362 and application processing circuitry 370 can be configured to store information in memory, operate the system 100, and receive and send information in the form of signals between the onboard communication module connected to the CPU 250, the controller 362, the weight data AI analytics programs 170 and the data lake 360. The weight data AI analytics programs 170 may analyze the data from the data lake by looking for patterns related to the search queries, unknown correlations, market trends and customer preferences. In a non-limiting example, the patterns may be the relationship of the weight gain over a time period to caloric information of restaurant food the vehicle seat occupant has visited frequently, finding lower calorie options, finding fitness centers in a locational range, finding weight loss physicians, dieticians or centers which specialize in weight management and generate a weight analysis record which is sent to the weight analysis processor 372. The weight analysis processor may retrieve the subscriber data from the subscriber database 367, correlate the weight analysis record with the user profile, and transmit the correlation to the weight management recommendation module 374. The weight management recommendation module 374 receives the correlation and generates a weight management recommendation as to a treatment for the weight condition at recommendation module 374. The recommendation is fed back to the controller 362, which transmits the recommendation to the CPU 250 of the vehicle 140. The CPU 250 provides the recommendation as feedback to the occupant and updates the memory 252. If the occupant has downloaded the weight management application on his/her own smart device, the application may communicate the recommendation back to the occupant by email, messaging, onto the screen of the app on the smart device or the like.

The controller 362 receives data communications from the on-board communication module 210 of the vehicle 104. The controller 362 also receives GPS data 212, data entered at graphical user interface 208 and data from data lake 360. The controller may send a search query to the data lake for historical and/or predictive information relevant to the type of weight condition (weight gain/loss). Based on the query, the data lake may return information regarding weight management, such causes and treatments related to the weight condition. The data lake may also provide product listings, preferred lists of medical professionals, weight care professionals, and the like.

FIG. 3B depicts how the data lake 360 and weight data analytics 370 are implemented in the data center 130. The data lake 360 stores the records of all the images and weight conditions sourced from the connected vehicles 140, along with recommendations made. The data lake is also connected to a plurality of databases, such as medical databases 361A, links to product websites 361B, weight management professional databases 361C, weight research blogs 361D, fitness management databases 361E. The data lake may additionally link to weight management articles 361G, and other databases 361F, hospital 361I, or relevant links, which may be websites, new articles, social media, or the like. The data lake may also link to lists of emergency services in the current location of the connected vehicle, which may be accessed if the weight analysis indicates a high BMI conjunction with increased heart rate as sensed by a vehicle heart rate sensor.

Weight data AI analytics 370 analyzes the weight condition report from the connected vehicle 140 and creates search queries, which are transmitted to the data lake 360. The data lake retrieves the requested information and transmits the information back to the weight data AI analytics 370, which performs an analysis of the information. The data lake may then store weight data retrieved by the search queries with the records of the weight conditions, along with treatments and recommendations made for the weight conditions in the unstructured data.

Figure 4:
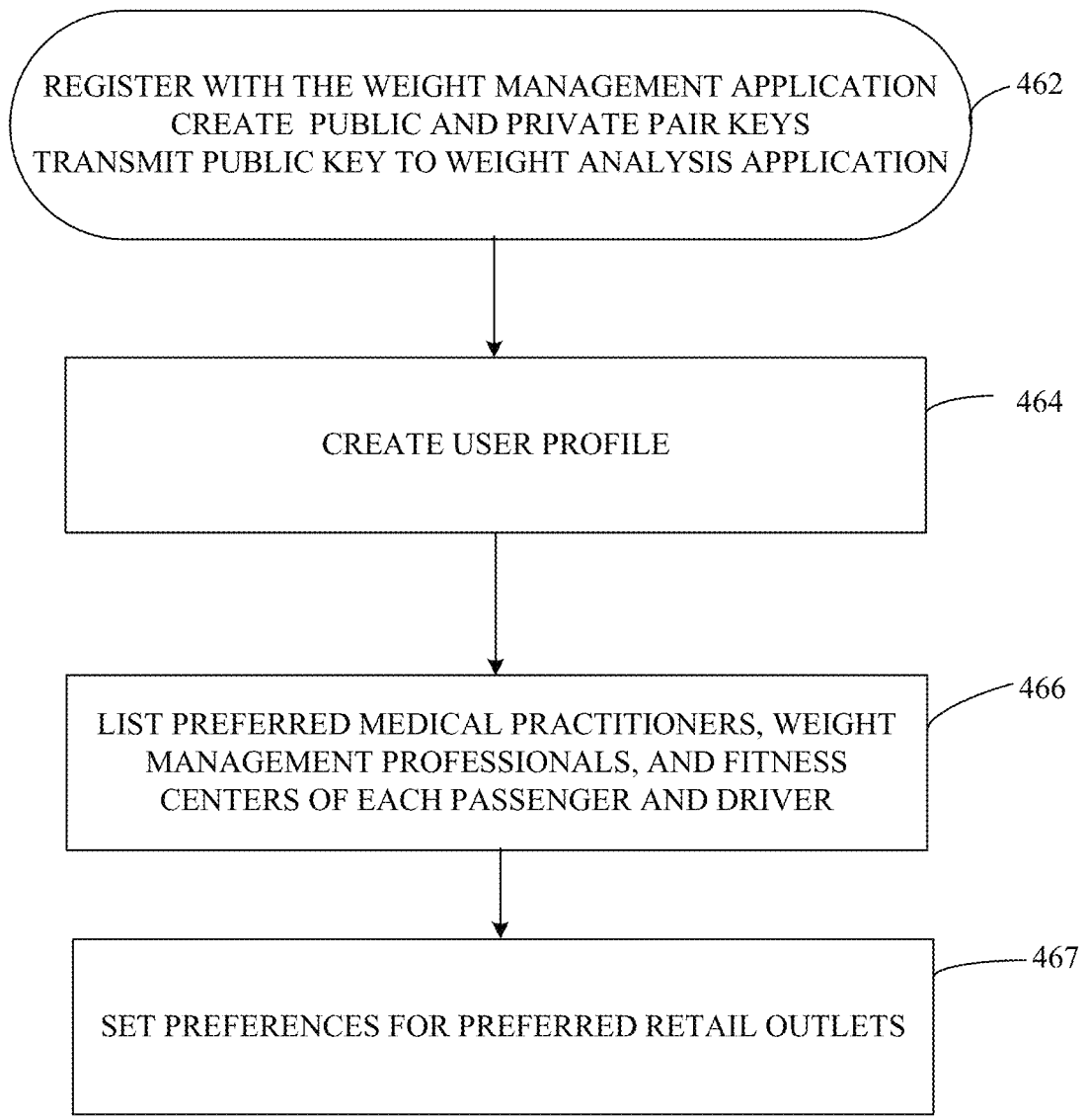
FIG. 4 is an exemplary flowchart of the weight management application registration process, according to certain embodiments.

FIG. 4 describes the process of registering a vehicle or the smart device of a vehicle seat occupant with the weight management application 165. Registration 462 may entail downloading the weight management application to a smart computing device of a vehicle seat occupant or to the CPU 210 through the onboard communication module 210. Registration comprises the creation of public and private pair keys by the vehicle computing system or smart device of the vehicle seat occupant, and transmitting the public key to the weight management application. Registration may be for a single user, a family or a group of users. In a non-limiting example, the owner of a connected vehicle may register his/her family with the smart application and set up user profiles for each family member. In a second non-limiting example, a company may offer the weight management application to a group of employees in a wellness program.

Registration 462 with the weight management application 165 may be free or may require a subscription fee. The weight analysis module 255 may be pre-registered and/or provided with a new vehicle or may be part of an upgrade purchase.

Each user, such as the owner, driver or a passenger, may create a user profile 464. The user profile may be for a single user, a family or a group of users. The user profile includes the name of the user, age, height, weight, ethnic origins, address, credit card information and known medical or weight conditions. The user profile may include a fingerprint. A fingerprint may be obtained by a fingerprint reader on the steering wheel or at the user interface 208. The user profile may include a facial image and/or body scan of the user taken at the time of registration, which is taken by a vehicle camera or uploaded from a computer or smart device of the user. The breath, voice, retinal scan, voice recording of a user may be received at other sensors 206, which may include a breathalyzer, retinal scanner or a voice recorder.

A list of preferred medical doctors, dieticians, fitness centers and weight care professionals of each vehicle seat occupant is stored at step 466. Additionally, preferences for preferred retail outlets are set. The weight management application 165 may search the marketplace websites of the preferred retail outlets for recommended weight products and notify the user of the availability of a weight care product and compare pricing. The weight management application may ask the user if he/she wishes to purchase the product and perform the purchase for the user.

An additional method for monetization of the weight analysis computer application includes providing sponsored content to a user of the computer application. The sponsored content is provided for use with the weight analysis computer application. A provider of the computer application is compensated in connection with provisioning the sponsored content for use with the computer application. For example, the weight management application may link the user to preferred medical practitioners, weight care professionals, fitness centers, retail outlets carrying weight management products or to websites of recommended weight management products who have signed a contractual agreement with the provider of the weight management application. The medical practitioners, weight care professionals, fitness centers, retail outlets carrying weight management products or to websites of recommended weight management products must register with the weight management application and pay a fee to be placed on the recommended lists. The present disclosure is not limited to the websites and databases 361A-361I listed above and shown in FIG. 3B, which are only a few exemplary instances.

Figure 5A:
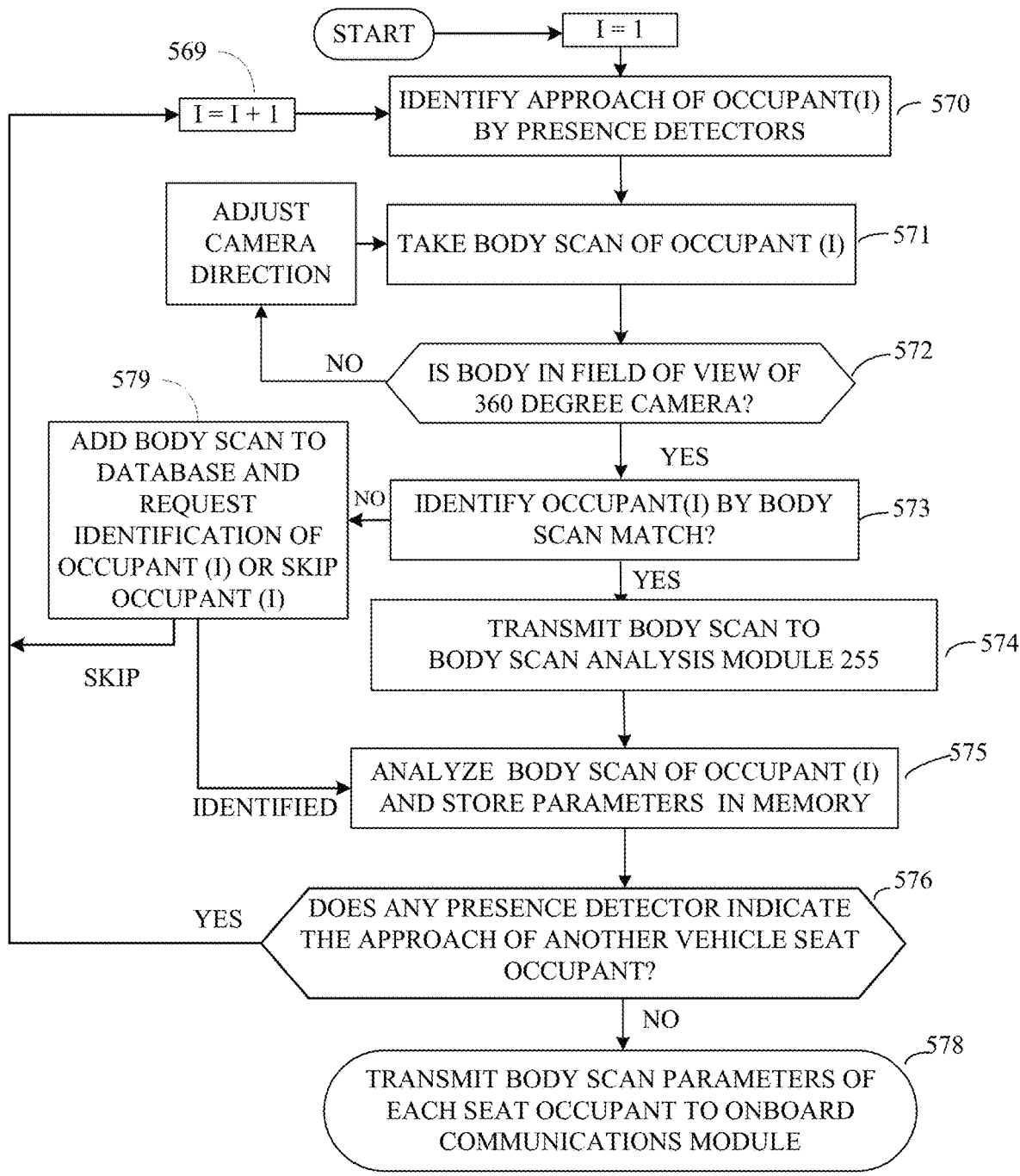
FIG. 5A is an exemplary flowchart of a process for taking a body scan of an approaching vehicle seat occupant.

FIG. 5A illustrates a flowchart of the process for taking a body scan of a future vehicle occupant. To start the body scan, the approach of an occupant (I, where I=1) of the vehicle (driver or passengers) is determined by vehicle presence detectors 207 ($207_1$, $207_2$, $207_3$, etc) which wake up 360 degree cameras 231. Cameras 231 and presence detectors 207 may be at the front, rear, on the roof or on the doors or sides of the vehicle. The vehicle may have a plurality of 360 degree cameras 231 and presence detectors 207 as shown in FIG. 2B. At step 571, the camera nearest the occupant (as determined by the strength of the signals of the presence detectors) takes body scan images of the occupant. At step 572, if the body of the occupant (I) is not in the field of view of the camera, the camera direction is adjusted and the image is retaken. Alternatively, the CPU 250 of the vehicle may request over a speaker that the vehicle seat occupant stand in a specific location or turn around during the body scan. The image is processed by the image processor 256 and compared to stored images in memory 252 which identifies registered vehicle seat occupants of the vehicle. If the occupant is identified by the match at step 573, the process moves to step 574, where the body scan of the occupant (I) is analyzed. If the occupant cannot be identified by matching the body scan, such as in the case of a new occupant, an identification of the occupant is requested, such as by a voice prompt or a message on the display 208. If the vehicle seat occupant is identified, the body scan is added to the memory 252 with the identification of the occupant (I). If an unidentified occupant (1) does not respond with identification as at step 579, the body scan is skipped and the process moves to step 569, where (I) is incremented by one and the process moves to occupant (2) (step 570). At step 574, the body scan is transmitted to the body scan analysis module 257. At step 575, the body scan analysis module 257 further determines parameters of the body scan, such as such as apparent weight, height, BMI, waist thickness, and other body dimensions. The body scan analysis module may determine that the vehicle seat occupant has gained or lost weight by comparing the body scan parameters at step 573 with historical parameters of occupant (I) stored in memory 252. The body scan parameters are stored in memory. At step 576, the process checks whether the presence detectors indicate the approach of another potential vehicle seat occupant. If there are no more seat occupants, the scanning process stops. If YES, the process moves to step 569, where (I) is incremented by one. At step 578, the body scan parameters of each vehicle seat occupant are transmitted to the onboard communications module for delivery to the data lake and/or the weight management application.

Figure 5B:
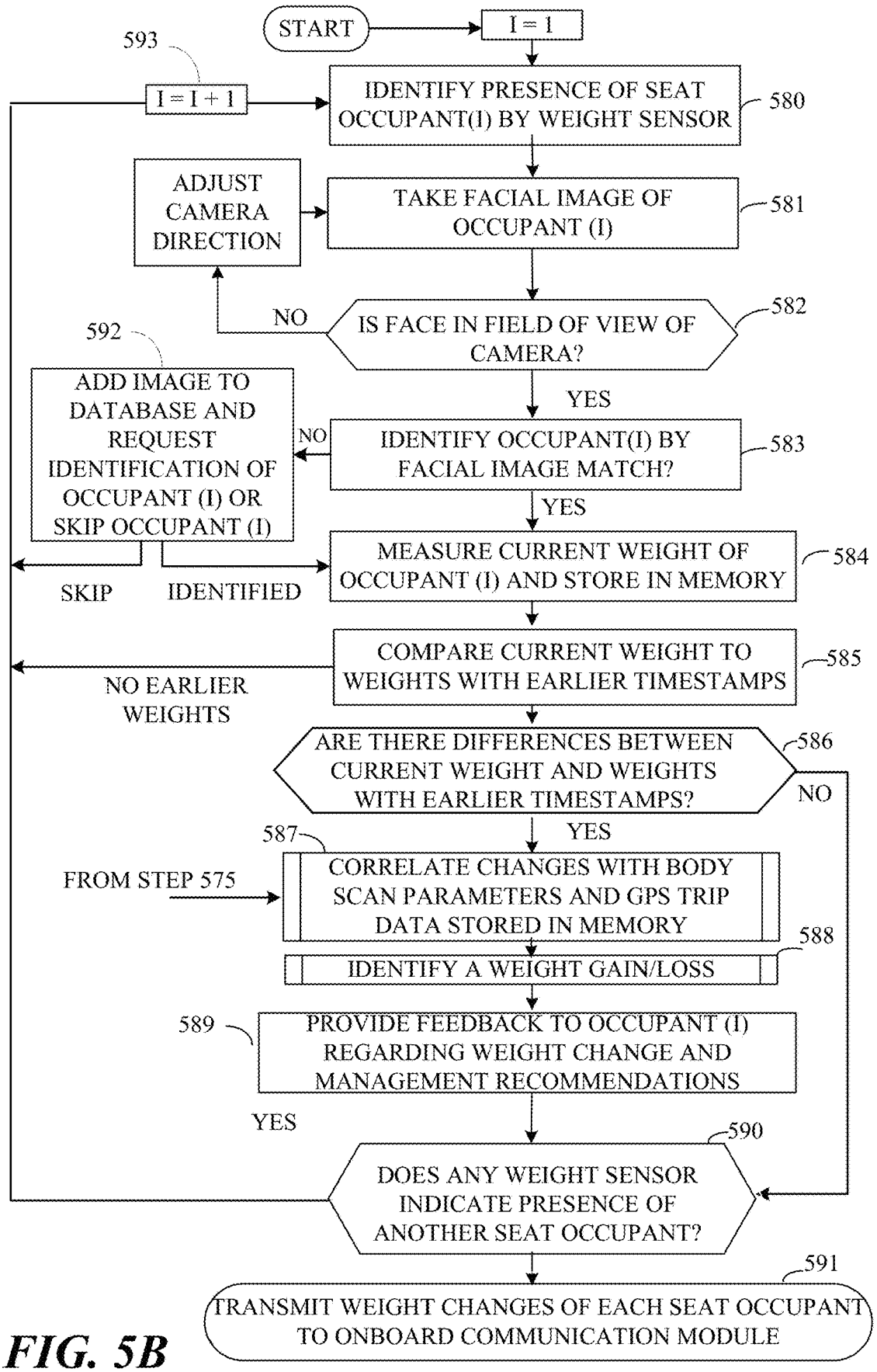
FIG. 5B is an exemplary flowchart of a process for identifying a vehicle seat occupant seated in a vehicle as illustrated in FIG. 2A, 2B by using one or more vehicle cameras, according to certain embodiments.

FIG. 5B illustrates a process for identifying further identifying a vehicle seat occupant. The body scan may not positively identify the seat occupant, or a passenger may sit in any number of seats after entering the vehicle, thus a secondary identification may be made to correctly store the weight as determined by the weight sensor 202. To start the weight analysis, the presence of a first occupant (I, where I=1) of the vehicle (driver or passengers) is determined by vehicle sensors, such as weight sensors 202, at step 580. The weight sensor 202 in the vehicle seat signals the presence of a seat occupant (I) in the seat, as illustrated in FIG. 2A, 2B. An in-vehicle camera ($232_1, 232_2, 232_3, \ldots, 232_k$) takes the facial image of the seat occupant (I) at step 581. At step 582, if the face is not in the field of view of the camera, the camera angle is adjusted and the facial image is retaken. If the face is in the field of view of the camera (step 583), the image is processed by the image processor 256 and compared to stored facial images which identify registered occupants of the vehicle. If a match is not found, the facial image is added to the database in memory 252 and the CPU requests through the user interface display or through audio that the seat occupant (I) provide identifying information at step 592. The driver or the seat occupant may tell the weight analysis module to skip occupant (I) if he/she is not a person of interest. For example, a driver giving a ride to a friend or a child's playmate may not wish to add the seat occupant (I) to the database.

At step 584, the current weight of seat occupant (I) is then acquired, timestamped and stored in memory 252. At step 585, the current weight is compared to earlier stored weights of the occupant (I) as determined by their timestamps. If there are no stored weights with earlier timestamps for the occupant (I), the process returns to step 593, where (I) is incremented by 1.

At step 586, the process determines whether there are differences between the earlier timestamped weights and the current weight. If NO, then the process moves to step 590 to determine whether the sensors detect another seat occupant. If further seat occupants are detected (YES), then the occupant number is incremented and the process returns to step 580. If no further seat occupants are detected (NO), the weight changes of each seat occupant are stored in memory and also transmitted to the onboard communication module 210 at step 591 for further analysis of the causes and treatments of the weight gain/loss by the weight management application 365.

At step 586, if there are no differences between the stored weight and current weight (NO), the process moves to step 590 to either increment I or to At step 586, if there are differences between the stored weight and current weight (YES), process moves to step 587. At step 587, the weight changes are correlated GPS trip data and with the stored body scan parameters from step 575 of FIG. 5A. At step 588, a weight gain/loss is identified by the weight analysis module 255. A treatment recommendation is generated at step 589 and delivered to the vehicle seat occupant (I). The treatment options may be determined by correlating the weight gain with trip data stored in the memory to identify places of business visited by the seat occupant over the last weeks or months which may have contributed to the weight gain/loss. The weight analysis module 255 may identify treatment options for the weight condition and deliver feedback to the occupant through a speaker 222, the user interface 208, as an SMS message to a cell phone, by an email, or the like.

At step 590, a determination is made as to whether the sensors detect another seat occupant. If further seat occupants are detected, then the seat occupant number is incremented. If no further seat occupants are detected, the identity, weight changes, GPS trip data and treatment recommendations of each seat occupant are stored in memory and also transmitted at step 591 to the onboard communication module for transmission with the body scan parameters in a data packet to the weight management application 365 for further analysis in order to improve the weight management recommendation.

Figure 6:
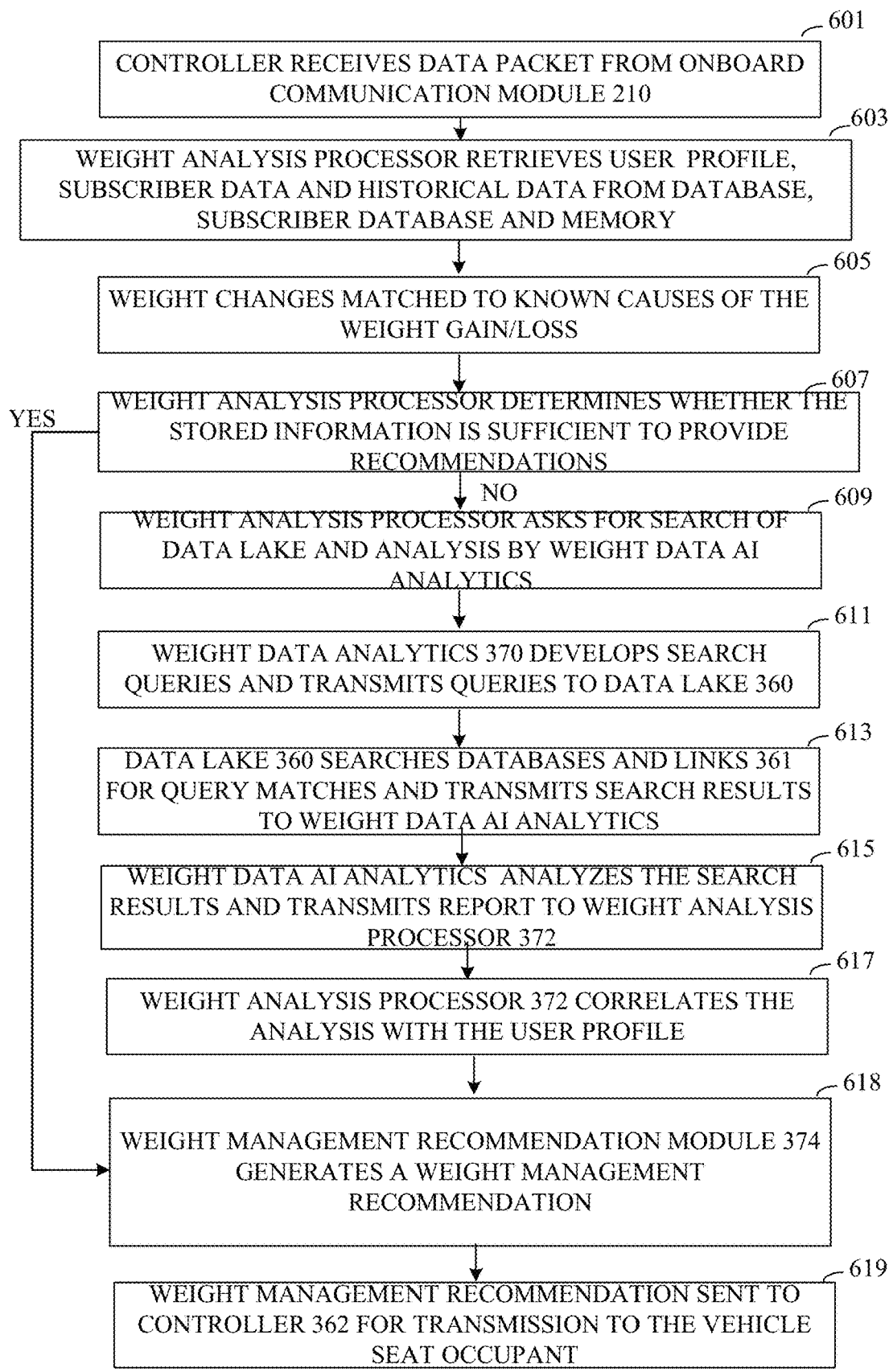
FIG. 6 is an exemplary flowchart of the process by which a body weight and set of body scan parameters is analyzed by the weight management application, according to certain embodiments.

FIG. 6 is a flowchart detailing the process by which the data packet from vehicle 140 is further analyzed by the weight management application 365 at the data center 330.

At step 601, the controller 362 receives the data packet from onboard communication module 210. At step 603, the weight analysis processor 365 retrieves the vehicle seat occupant user profile, subscriber data and historical data from database 364, subscriber database 367 and memory 368 respectively. At step 605, the weight analysis processor matches the weight changes and body scan parameters to known causes of the weight gain/loss condition. At step 607, the weight analysis processor determines whether the stored information is sufficient to provide recommendations. If YES, the process moves to step 619 in which treatment recommendations are made. If NO, the process moves to step 609, where the weight analysis processor recommends searching for more information by weight data AI analytics 370. At step 611, the weight data AI analytics module develops search queries and transmits the queries to the data lake 360. At step 613, the data lake 360 searches unstructured data, databases and links 361a-361l for query matches and transmits the search results to the weight data AI analytics module. At step 615, the weight data trained AI analytics module sifts the search results for patterns, correlations and related information and generates an analysis report, which is sent to weight analysis processor 372. At step 617, the weight analysis processor 372 correlates analysis with the user profile information. At step 618, the weight management recommendation module 374 generates a weight management recommendation, which is sent to controller 362 at step 619 for transmission to the vehicle seat occupant and/or CPU 250.

Weight management recommendations can include a report of the current weight, weight gain/loss, causes for the weight gain/loss, treatments of the weight gain/loss and recommendations to weight care professionals, medical practitioners, fitness centers, exercise trainers and products for treating the weight gain/loss. The weight management recommendations may include location and contact information for the weight care professionals, dieticians, medical practitioners, fitness centers and exercise trainers and lists of retail outlets which carry weight management products. The location and contact information may be for weight care professionals, medical practitioners, fitness centers and exercise trainers and retail outlets located near the home or current location of the vehicle seat occupant. The location and contact information may further contain emails or links to websites of the weight care professionals, medical practitioners, fitness centers and exercise trainers and retail outlets.

The first embodiment is illustrated with respect to FIG. 1 through FIG. 6. The first embodiment describes a method for managing the weight of a vehicle seat occupant using vehicle cameras and vehicle weight sensors, comprising detecting an approach of the vehicle seat occupant to the vehicle and generating a presence signal (by presence detector 207, FIG. 2A; step 570, FIG. 5A), performing a body scan (step 571) of the vehicle seat occupant upon receiving the presence signal (by 360 degree camera 231, FIG. 2A; step 571, FIG. 5A), determining a set of body scan parameters from the body scan of the vehicle seat occupant (step 575), recording a sensor signature of the vehicle seat occupant (step 581, FIG. 5B), identifying the vehicle seat occupant by matching the sensor signature to a set sensor signatures of registered vehicle seat occupants stored in the vehicle memory (step 583), measuring a current body weight of the vehicle seat occupant (step 584, FIG. 5B), timestamping and storing the current body weight in the vehicle memory 252, determining changes between the current body weight and at least one stored body weight of the vehicle seat occupant having a timestamp recorded during an earlier time period (step 585), accessing GPS records venues visited by the vehicle seat occupant during the earlier time period (from GPS unit 212, FIG. 2A), correlating the weight changes, the set of body scan parameters and the GPS records of venues visited with weight information stored in the vehicle memory (step 587) to generate a weight analysis, generating a weight management recommendation from the weight analysis (step 589), notifying the vehicle seat occupant of the weight management recommendation, updating the vehicle memory 252 with the weight management recommendation, and transmitting the body weight changes (step 578) and the body scan parameters (step 591) to a data lake 160.

The method includes comparing the current body weight and at least one stored body weight of the vehicle seat occupant having a timestamp recorded during an earlier time period selected from at least one of greater than two weeks and less than five years before the current weight, greater than one month and less than three months before the current weight, and greater than six months and less than one year before the current weight.

Alternatively, the method includes comparing the current body weight with each body weight from an earlier time period until one of a change is detected and all body weights having earlier timestamps have been compared to the current body weight.

The method includes comparing each set of current body scan parameters with at least one previous set of body scan parameters having body scan parameters timestamps in a range in a range selected from at least one of greater than two weeks and less than five years before the current weight, greater than one month and less than three months before the current weight, and greater than six months and less than one year before the current weight.

Alternatively, the method includes comparing the current set of body scan parameters with each previous set of body scan parameters until one of a change is detected and all previous sets of body scan parameters have been compared to the current set of body scan parameters.

The method further includes recording the sensor signature by at least one of an internal vehicle camera 232, an audio sensor, a fingerprint sensor 204, and a retinal sensor (other sensors 206, FIG. 2A).

The method further includes registering the vehicle with a weight management application by creating public and private pair keys in a vehicle computing system of the vehicle, transmitting the public key to the weight management application, creating a user profile for each vehicle seat occupant including at least a facial image, an age, a height, a weight, a gender, an ethnic group, an address, a credit card number and medical diseases of the vehicle seat occupant, and providing lists of preferred medical practitioners, dieticians, weight management centers, fitness centers and scalp care professionals and retail outlets of each vehicle seat occupant.

The method continues by combining the vehicle seat occupant identification, the body weight changes, the set of body scan parameters and the GPS records of venues visited into a data packet and transmitting the data packet to the weight management application 365.

At the weight management application, the method includes receiving the data packet (by transceiver 366, requesting, by the weight management application, a search related to the vehicle seat occupant body weight changes, the set of body scan parameters and the GPS records of venues visited, receiving the request by a weight data artificial intelligence (AI) analytics module 370, querying the data lake 360 for information relating to the vehicle seat occupant body weight changes, the set of body scan parameters and the GPS records of venues visited, searching, by the data lake, unstructured data and structured databases for matches to the query, receiving, by the weight data AI analytics module, the matches to the query, analyzing, by the weight data AI analytics module, the matches to determine weight conditions, treatment options for the weight conditions and at least one of weight loss or weight gain product information related to the weight conditions, generating, by the weight data AI analytics module, a weight report, providing the weight report to the weight management application for correlation with the vehicle seat occupant user profile, generating a weight management recommendation (at weight management recommendation module 374, transmitting the weight management recommendation to the vehicle, updating the vehicle memory 252, and delivering the weight management recommendation to the vehicle seat occupant.

Additionally the method can include registering a smart device of the vehicle seat occupant with the weight management application 365, by creating public and private pair keys (step 462, FIG. 4) with a smart device of the vehicle seat occupant, transmitting the public key to the weight management application, creating a vehicle seat occupant user profile 464 including at least a facial image, an age, a height, a weight, a gender, an ethnic group, an address, a credit card number and previous weight and medical diseases of the vehicle seat occupant, and providing a list of preferred weight management professionals, dieticians, weight management centers, fitness centers and retail outlets. This method includes receiving, by the weight management application, the data packet, requesting, by the weight management application, a search related to the vehicle seat occupant weight information record, receiving the request by a weight data artificial intelligence (AI) analytics module 370, querying the data lake 160 for information relating to the vehicle seat occupant body weight changes, the set of body scan parameters and the GPS records of venues visited, searching, by the data lake, unstructured data and structured databases (361-A to 361-1, FIG. 3B) for matches to the query, receiving, by the hair and scalp data AI analytics module, the matches to the query, analyzing, by the weight data AI analytics module, the matches to determine weight conditions, treatment options for the weight conditions and at least one of weight loss or weight gain product information related to the weight conditions, generating, by the weight data AI analytics module, a weight report, providing the weight report to the weight management application for correlation with the vehicle seat occupant user profile 467, generating a weight management recommendation, transmitting the weight management recommendation to the smart device of the registered vehicle seat occupant.

Providing a weight management recommendation to the vehicle seat occupant further comprises at least one of recommending a medical practitioner based on a home location or a current location of the vehicle seat occupant, recommending a dietician based on a home location or a current location of the vehicle seat occupant, recommending a weight management center based on a home location or a current location of the vehicle seat occupant, recommending a fitness center based on a home location or a current location of the vehicle seat occupant, recommending a fitness trainer based on a home location or a current location of the vehicle seat occupant, recommending weight management products, recommending retail websites of weight management products, recommending retail outlets for weight management products based on a home location or a current location of the vehicle seat occupant, recommending an exercise program, recommending low calorie restaurants based on a home location or current location of the vehicle seat occupant and the restaurant visit frequency record, and recommending a weight management regime.

The second embodiment is illustrated with respect to FIG. 1 through FIG. 6. The second embodiment describes a system for managing the weight of a vehicle seat occupant, comprising a plurality of vehicles ($140_1$-$140_n$, FIG. 1), each vehicle including: at least one presence detector 207 external to the vehicle and capable of detecting the approach of a vehicle seat occupant and sending a presence signal, at least one 360 degree camera 231 external to the vehicle and configured for performing a body scan of the vehicle seat occupant upon receiving the presence signal, an image processor 251 configured for receiving and timestamping the body scan, a body scan analysis module 257 configured for determining a set of current body scan parameters from the body scan, at least one internal vehicle sensor (204, 206, 231, FIG. 2A) configured for recording a sensor signature of the vehicle seat occupant, wherein the internal vehicle sensor is at least one of a plurality of cameras (231), an audio sensor, a fingerprint sensor and a retinal sensor, at least one vehicle seat weight sensor 202 configured for measuring a current body weight of the vehicle seat occupant, a weight processor 251 configured to receive the current body weight and timestamp the body weight, a memory 252 including a first database configured for storing, for each vehicle seat occupant, a user profile, at least one sensor signature, timestamped body scans, timestamped weight measurements and a second database configured for storing information related to weight management.

The system further includes an identity module 254 configured for identifying the vehicle seat occupant by matching the sensor signature to a sensor signature stored in the first database, a weight comparison module 253 configured for determining changes between the current body weight and at least one stored body weight of the vehicle seat occupant having a timestamp recorded during an earlier time period, a GPS unit 212 configured for generating trip information regarding venues visited by the vehicle seat occupant, central processing unit (CPU) 250 operatively connected to the GPS unit 212 and configured for accessing GPS trip information regarding venues visited by the vehicle seat occupant during the earlier time period, a weight analysis module 255 configured for generating a weight management recommendation by correlating the set of body scan parameters, the weight changes and the trip information of venues visited during the earlier time period with the information related to weight management, a user interface configured for delivering the weight management recommendation to the vehicle seat occupant, wherein the CPU is further operatively connected to the at least one presence detector, the at least one 360 degree camera, the at least one vehicle seat weight sensor, the at least one internal vehicle sensor, the vehicle memory, the body scan analysis module, the image processor, the weight processor, the weight comparison module, the weight analysis module, the identity module and an onboard communications module, wherein the onboard communications module is configured for transmitting a first data packet including the set of body scan parameters, the weight changes, the vehicle seat occupant identity and the GPS trip information regarding venues visited and for transmitting a second data packet including the set of body scan parameters, the weight changes, a set of anonymized information of the user profile and the GPS trip information regarding venues visited to a data lake 360.

The at least one internal vehicle sensor can include a plurality of interior cameras ($232_1$, . . . , $232_n$, FIG. 2B), each camera having a field of view focused at the level of a face of a vehicle seat occupant, each camera configured to record a facial record of the vehicle seat occupant.

The system further comprises a weight management application 365 located in a data center 130. The weight management application includes a registration module 363 configured for registering each vehicle of the plurality of vehicles with the weight management application, a transceiver 366 configured for receiving the first data packet from the onboard communications module of each vehicle, a weight analysis processor 372 configured for requesting a search related to the body weight changes, the set of body scan parameters and the GPS records of venues visited of each vehicle seat occupant, wherein the data center includes a weight data artificial intelligence (AI) analytics module 370 configured to receive the request and generate search queries related to the body weight changes, the set of body scan parameters and the GPS records of venues visited of each vehicle seat occupant, wherein the data lake 360 is configured to receive the search queries and conduct the search of unstructured data and structured databases for matches to the queries, wherein the weight data AI analytics module is further configured to analyze the matches to determine weight conditions, treatment options for the weight conditions and at least one of weight loss or weight gain product information related to the weight conditions and to generate a weight report.

The weight analysis processor 372 is further configured to correlate the weight report with the vehicle seat occupant user profile (either from database 364 or from vehicle memory 252). A weight management recommendation module 374 is configured to generate a vehicle seat occupant weight management recommendation, wherein the transceiver 366 is further configured to transmit the vehicle seat occupant weight management recommendation to the respective onboard communications module 210 of the vehicle occupied by the vehicle seat occupant.

The weight management recommendation further includes at least one of recommending a medical practitioner based on a home location or a current location of the vehicle seat occupant, recommending a weight management professional based on a home location or a current location of the vehicle seat occupant, recommending a dietician based on a home location or a current location of the vehicle seat occupant, recommending a weight management center based on a home location or a current location of the vehicle seat occupant, recommending a fitness center based on a home location or a current location of the vehicle seat occupant, recommending weight management products, recommending retail websites of weight management products, recommending retail outlets for weight management products based on a home location or a current location of the vehicle seat occupant, recommending an exercise program, recommending low calorie restaurants based on a home location or current location of the vehicle seat occupant and the restaurant visit frequency record, and recommending a weight management regime.

The weight management application further comprises an application memory 368 including a first database 367 of subscriber information, the subscriber information including a user profile of each vehicle seat occupant of each of the plurality of vehicles, a second database of sponsored content 364, wherein the sponsored content includes lists of medical practitioners, weight management professionals, dieticians, fitness centers, fitness trainers, weight management products, retail websites or retail outlets for purchasing weight management products and restaurants in the home location or current location of the vehicle seat occupant, and wherein the registration module 363 is further configured to register sponsors of weight related treatment or products.

The registration module is further configured to register a smart device of a vehicle seat occupant travelling in any of the plurality of vehicles with the weight management application by receiving a public key from the smart device (step 462, FIG. 4), requesting profile information (step 464) from the vehicle occupant including age, weight, gender, ethnic origins, previous weight and medical diseases of the vehicle seat occupant, requesting lists (steps 466-467) of preferred medical practitioners, weight management professionals, dieticians, weight management centers, fitness centers, fitness trainers, weight management products and retail outlets. The registration module is further configured to store the public key, personal information and lists in the application memory.

The weight management application 365 is further configured to wherein the weight management application is further configured to receive a body scan and current weight of the registered vehicle seat occupant whenever the vehicle seat occupant travels in any of the plurality of vehicles registered with the weight management application, perform an analysis of the body scan and detect body scan parameters, detect changes between a current body weight and at least one body weight of the vehicle seat occupant stored in the application memory having a timestamp recorded during an earlier time period, access GPS trip information regarding venues visited by the vehicle seat occupant during the earlier time period, request a search by the weight data AI analytics module of the data lake for information related to the body weight changes and the body scan of the registered vehicle seat occupant, wherein the weight data AI analytics module is further configured to receive the request and generate search queries related to the body weight changes, the set of body scan parameters and the GPS records of venues visited of the registered vehicle seat occupant, wherein the data lake is configured to receive the search queries and conduct the search of unstructured data and structured databases for matches to the queries, wherein the weight data AI analytics module is further configured to analyze the matches to determine weight conditions, treatment options for the weight conditions and at least one of weight loss or weight gain product information related to the weight conditions and to generate a weight report, wherein the weight analysis processor is further configured to correlate the weight report with the vehicle seat occupant user profile, wherein the weight management recommendation module is further configured to generate a weight management recommendation for the registered vehicle seat occupant, and wherein the transceiver is further configured to transmit the weight management recommendation to the smart device of the registered vehicle seat occupant.

The data lake is further configured to store the body weight, sets of body scan parameters and weight management recommendations of each of the identified vehicle seat occupants of each of the plurality of vehicles as unstructured data.

The third embodiment is illustrated with respect to FIG. 1 through FIG. 10. The third embodiment describes a non-transitory computer readable medium having instructions stored therein that, when executed by one or more processor, cause the one or more processors to perform for managing the weight of a vehicle seat occupant using vehicle cameras and vehicle weight sensors, comprising detecting an approach of the vehicle seat occupant to the vehicle and generating a presence signal (by presence detector 207, FIG. 2A; step 570, FIG. 5A), performing a body scan (step 571) of the vehicle seat occupant upon receiving the presence signal (by 360 degree camera 231, FIG. 2A; step 571, FIG. 5A), determining a set of body scan parameters from the body scan of the vehicle seat occupant (step 575), recording a sensor signature of the vehicle seat occupant (step 581, FIG. 5B), identifying the vehicle seat occupant by matching the sensor signature to a set sensor signatures of registered vehicle seat occupants stored in the vehicle memory (step 583), measuring a current body weight of the vehicle seat occupant (step 584, FIG. 5B), timestamping and storing the current body weight in the vehicle memory 252, determining changes between the current body weight and at least one stored body weight of the vehicle seat occupant having a timestamp recorded during an earlier time period (step 585), accessing GPS records venues visited by the vehicle seat occupant during the earlier time period (from GPS unit 212, FIG. 2A), correlating the weight changes, the set of body scan parameters and the GPS records of venues visited with weight information stored in the vehicle memory (step 587) to generate a weight analysis, generating a weight management recommendation from the weight analysis (step 589), notifying the vehicle seat occupant of the weight management recommendation, updating the vehicle memory 252 with the weight management recommendation, and transmitting the body weight changes (step 578) and the body scan parameters (step 591) to a data lake 160.

The non-transitory computer readable medium method includes registering the vehicle with a weight management application by creating public and private pair keys in a vehicle computing system of the vehicle, transmitting the public key to the weight management application, creating a user profile for each vehicle seat occupant including at least a facial image, an age, a height, a weight, a gender, an ethnic group, an address, a credit card number and medical diseases of the vehicle seat occupant, and providing lists of preferred medical practitioners, dieticians, weight management centers, fitness centers and scalp care professionals and retail outlets of each vehicle seat occupant.

The non-transitory computer readable medium method continues by combining the vehicle seat occupant identification, the body weight changes, the set of body scan parameters and the GPS records of venues visited into a data packet and transmitting the data packet to the weight management application 365. At the weight management application, the non-transitory computer readable medium method includes receiving the data packet (by transceiver 366, requesting, by the weight management application, a search related to the vehicle seat occupant body weight changes, the set of body scan parameters and the GPS records of venues visited, receiving the request by a weight data artificial intelligence (AI) analytics module 370, querying the data lake 360 for information relating to the vehicle seat occupant body weight changes, the set of body scan parameters and the GPS records of venues visited, searching, by the data lake, unstructured data and structured databases for matches to the query, receiving, by the weight data AI analytics module, the matches to the query, analyzing, by the weight data AI analytics module, the matches to determine weight conditions, treatment options for the weight conditions and at least one of weight loss or weight gain product information related to the weight conditions, generating, by the weight data AI analytics module, a weight report, providing the weight report to the weight management application for correlation with the vehicle seat occupant user profile, generating a weight management recommendation (at weight management recommendation module 374, transmitting the weight management recommendation to the vehicle, updating the vehicle memory 252, and delivering the weight management recommendation to the vehicle seat occupant.

Figure 7:
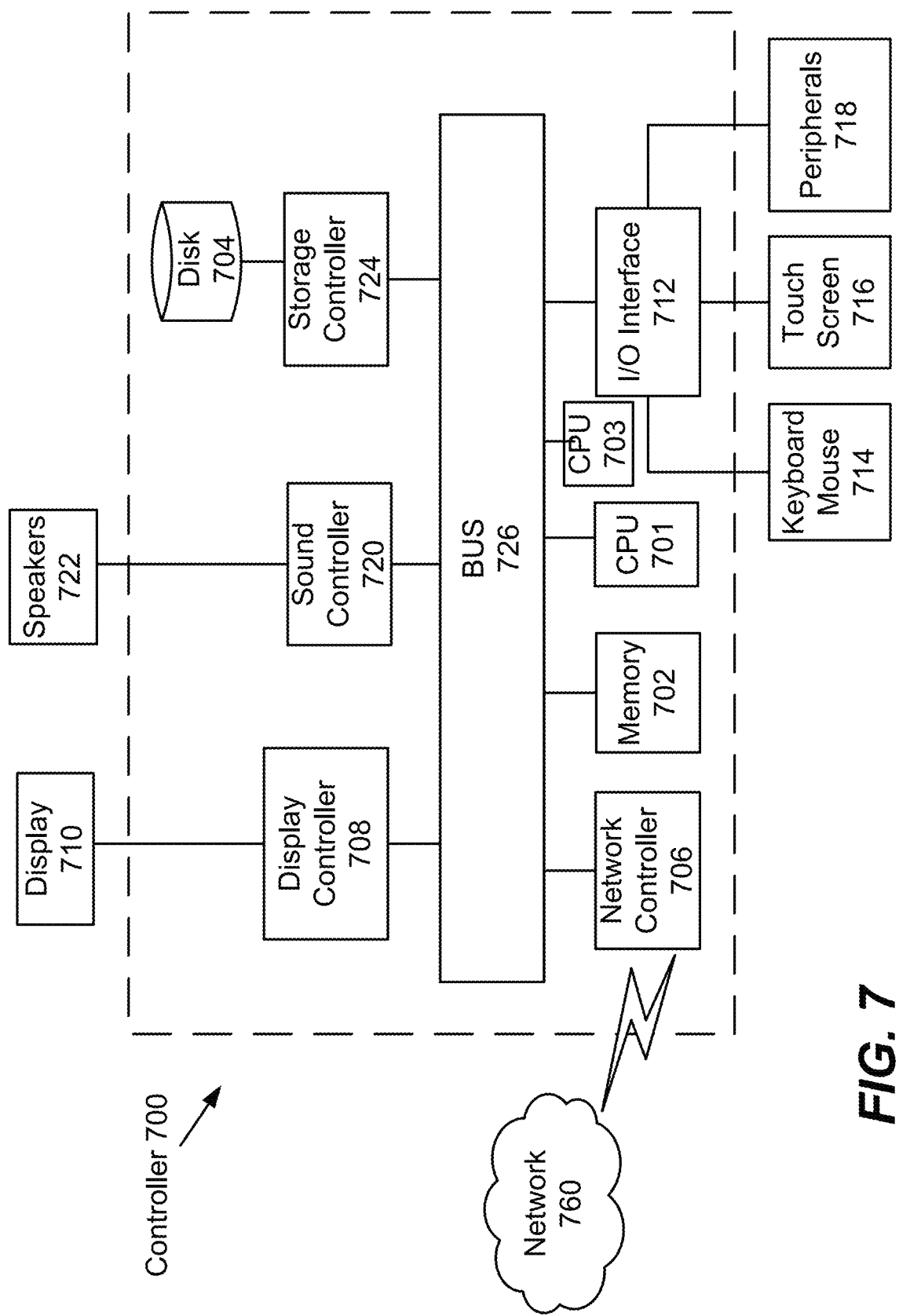
FIG. 7 is an illustration of a non-limiting example of details of computing hardware used in the computing systems, according to certain embodiments.

Next, further details of the hardware description of the computing environments of FIG. 2A and FIG. 3A according to exemplary embodiments are described with reference to FIG. 7. In FIG. 7, a controller 700 is described which is representative of the controller 250 of FIG. 1 or the controller 362 of FIG. 3A in which the controller 700 is a computing device which includes a CPU 701 which performs the processes described above/below. The process data and instructions may be stored in memory 702. These processes and instructions may also be stored on a storage medium disk 704 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 701, 703 and an operating system such as Microsoft Windows 7, UNIX, Solaris, LINUX, Apple MAC-OS and other systems known to those skilled in the art.

The hardware elements in order to achieve the computing device may be realized by various circuitry elements, known to those skilled in the art. For example, CPU 701 or CPU 703 may be a Xenon or Core processor from Intel of America or an Opteron processor from AMD of America, or may be other processor types that would be recognized by one of ordinary skill in the art. Alternatively, the CPU 701, 703 may be implemented on an FPGA, ASIC, PLD or using discrete logic circuits, as one of ordinary skill in the art would recognize. Further, CPU 701, 703 may be implemented as multiple processors cooperatively working in parallel to perform the instructions of the inventive processes described above.

The computing device in FIG. 7 also includes a network controller 706, such as an Intel Ethernet PRO network interface card from Intel Corporation of America, for interfacing with network 760. As can be appreciated, the network 760 can be a public network, such as the Internet, or a private network such as an LAN or WAN network, or any combination thereof and can also include PSTN or ISDN sub-networks. The network 760 can also be wired, such as an Ethernet network, or can be wireless such as a cellular network including EDGE, 3G, 4G and 5G wireless cellular systems. The wireless network can also be Wi-Fi, Bluetooth, or any other wireless form of communication that is known.

The computing device further includes a display controller 708, such as a NVIDIA GeForce GTX or Quadro graphics adaptor from NVIDIA Corporation of America for interfacing with display 710, such as a Hewlett Packard HPL2445w LCD monitor. A general purpose I/O interface 712 interfaces with a keyboard and/or mouse 714 as well as a touch screen panel 716 on or separate from display 710. General purpose I/O interface also connects to a variety of peripherals 718 including printers and scanners, such as an OfficeJet or DeskJet from Hewlett Packard.

A sound controller 720 is also provided in the computing device such as Sound Blaster X-Fi Titanium from Creative, to interface with speakers/microphone 722 thereby providing sounds and/or music.

The general purpose storage controller 724 connects the storage medium disk 704 with communication bus 726, which may be an ISA, EISA, VESA, PCI, or similar, for interconnecting all of the components of the computing device. A description of the general features and functionality of the display 710, keyboard and/or mouse 714, as well as the display controller 708, storage controller 724, network controller 706, sound controller 720, and general purpose I/O interface 712 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 8.

Figure 8:
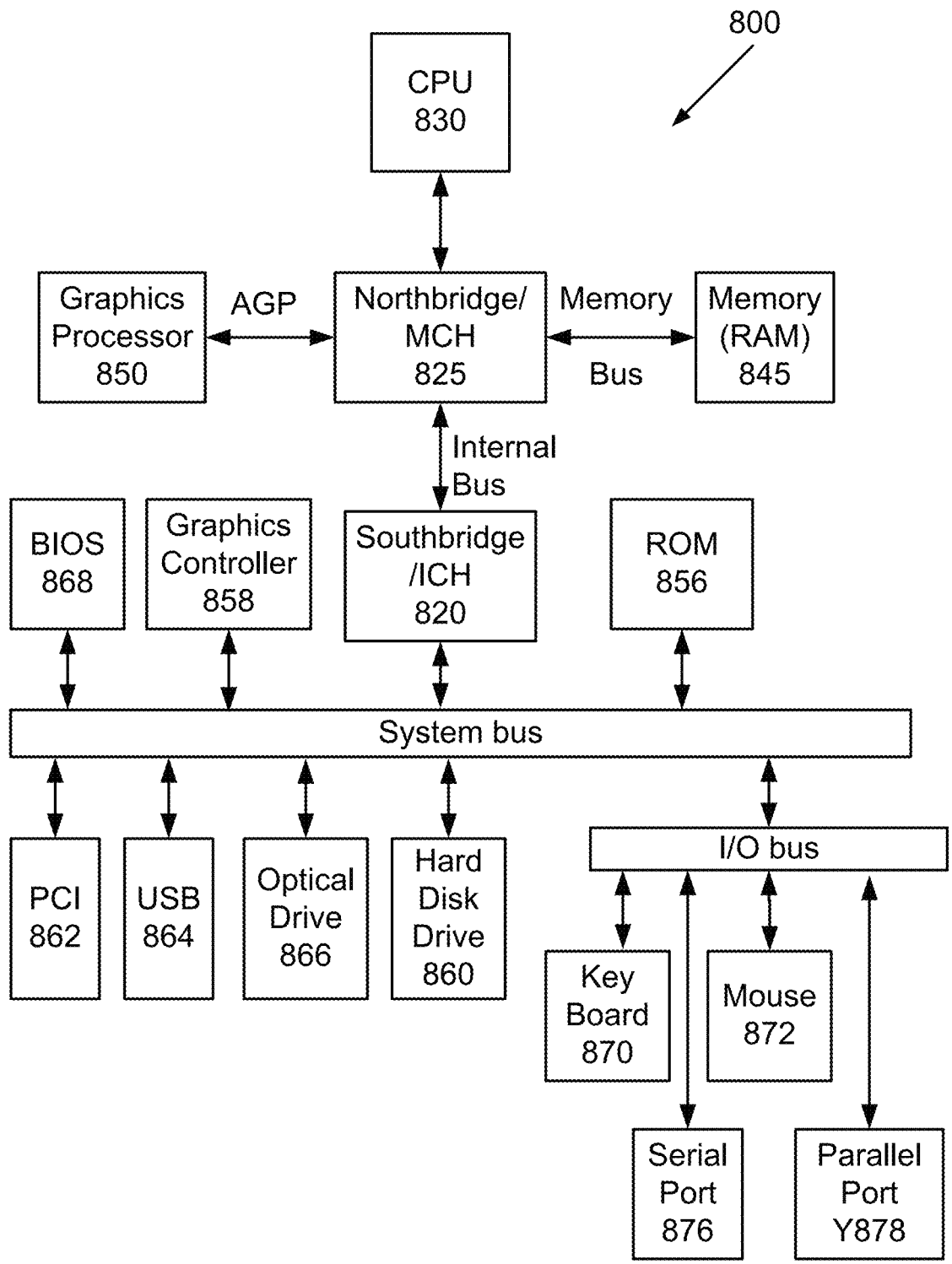
FIG. 8 is an exemplary schematic diagram of a data processing system used within the computing system, according to certain embodiments.

FIG. 8 shows a schematic diagram of a data processing system, according to certain embodiments, for performing the functions of the exemplary embodiments. The data processing system is an example of a computer in which code or instructions implementing the processes of the illustrative embodiments may be located.

In FIG. 8, data processing system 800 employs a hub architecture including a north bridge and memory controller hub (NB/MCH) 825 and a south bridge and input/output (I/O) controller hub (SB/ICH) 820. The central processing unit (CPU) 830 is connected to NB/MCH 825. The NB/MCH 825 also connects to the memory 845 via a memory bus, and connects to the graphics processor 850 via an accelerated graphics port (AGP). The NB/MCH 825 also connects to the SB/ICH 820 via an internal bus (e.g., a unified media interface or a direct media interface). The CPU Processing unit 830 may contain one or more processors and even may be implemented using one or more heterogeneous processor systems.

Figure 9:
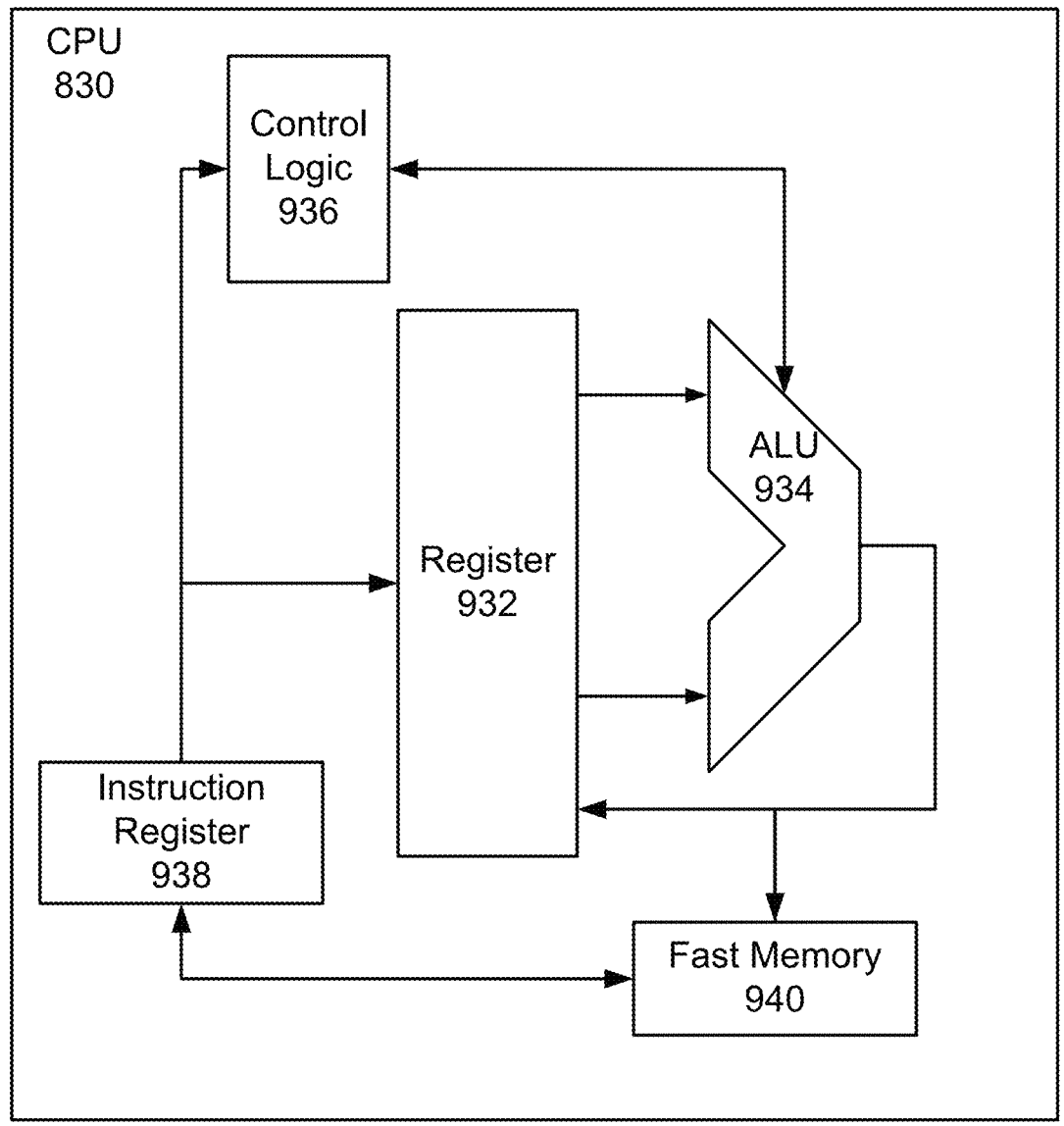
FIG. 9 is an exemplary schematic diagram of a processor used with the computing system, according to certain embodiments.

For example, FIG. 9 shows one implementation of CPU 830. In one implementation, the instruction register 938 retrieves instructions from the fast memory 940. At least part of these instructions are fetched from the instruction register 938 by the control logic 936 and interpreted according to the instruction set architecture of the CPU 830. Part of the instructions can also be directed to the register 932. In one implementation the instructions are decoded according to a hardwired method, and in another implementation the instructions are decoded according to a microprogram that translates instructions into sets of CPU configuration signals that are applied sequentially over multiple clock pulses. After fetching and decoding the instructions, the instructions are executed using the arithmetic logic unit (ALU) 934 that loads values from the register 932 and performs logical and mathematical operations on the loaded values according to the instructions. The results from these operations can be feedback into the register and/or stored in the fast memory 940. According to certain implementations, the instruction set architecture of the CPU 830 can use a reduced instruction set architecture, a complex instruction set architecture, a vector processor architecture, a very large instruction word architecture. Furthermore, the CPU 830 can be based on the Von Neuman model or the Harvard model. The CPU 830 can be a digital signal processor, an FPGA, an ASIC, a PLA, a PLD, or a CPLD. Further, the CPU 830 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 8, the data processing system 800 can include that the SB/ICH 820 is coupled through a system bus to an I/O Bus, a read only memory (ROM) 856, universal serial bus (USB) port 864, a flash binary input/output system (BIOS) 868, and a graphics controller 858. PCI/PCIe devices can also be coupled to SB/ICH 888 through a PCI bus 862. The PCI devices may include, for example, Ethernet adapters, add-in cards, and PC cards for notebook computers. The Hard disk drive 860 and CD-ROM 866 can use, for example, an integrated drive electronics (IDE) or serial advanced technology attachment (SATA) interface. In one implementation the I/O bus can include a super I/O (SIO) device.

Further, the hard disk drive (HDD) 860 and optical drive 866 can also be coupled to the SB/ICH 820 through a system bus. In one implementation, a keyboard 870, a mouse 872, a parallel port 878, and a serial port 876 can be connected to the system bus through the I/O bus. Other peripherals and devices that can be connected to the SB/ICH 820 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

Figure 10:
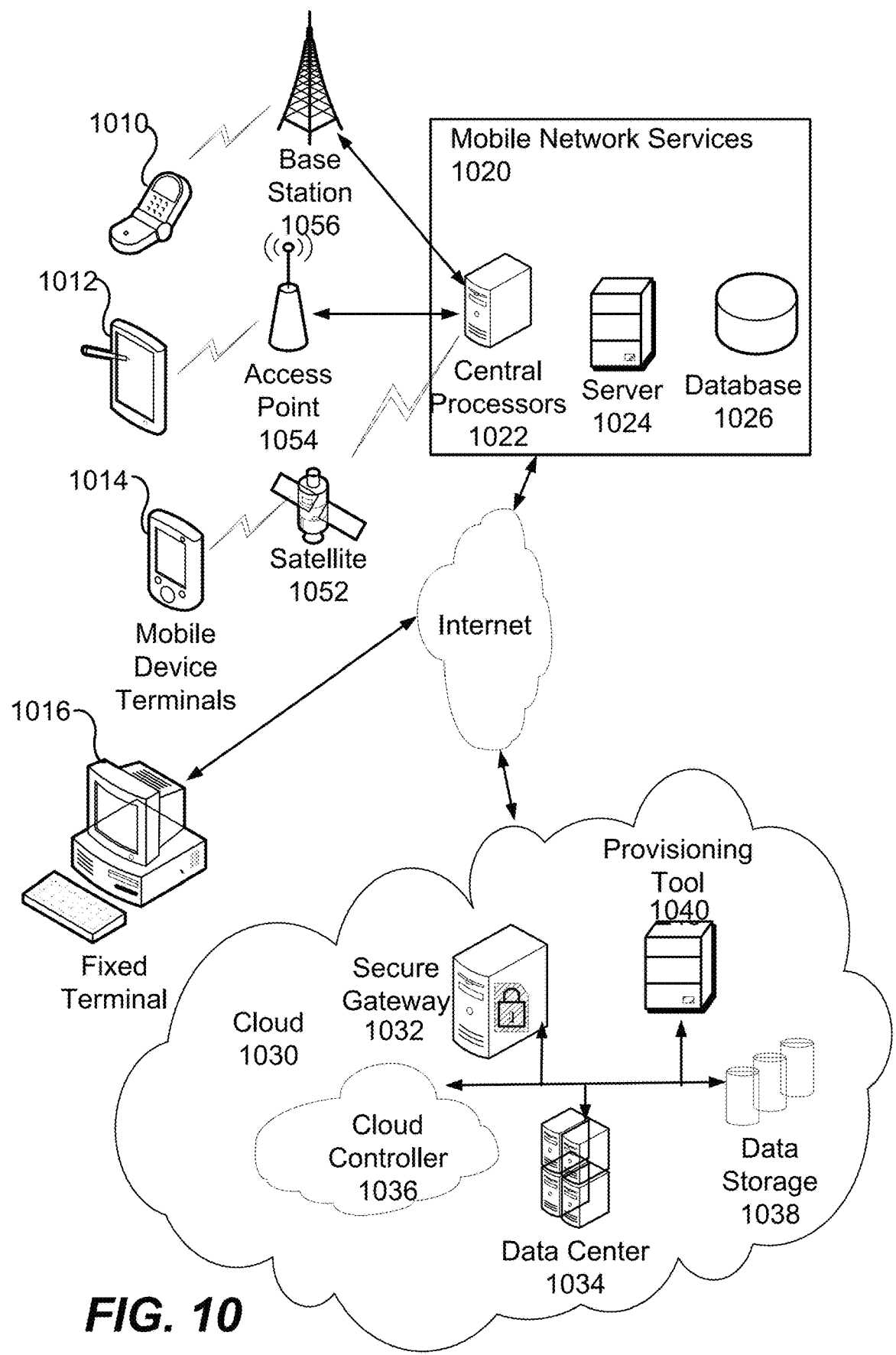
FIG. 10 is an illustration of a non-limiting example of distributed components which may share processing with the controller, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 10, in addition to various person interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A method for managing a weight of a vehicle seat occupant using vehicle cameras and vehicle weight sensors, comprising:
    detecting an approach of the vehicle seat occupant to the vehicle and generating a presence signal;
    performing a body scan of the vehicle seat occupant upon receiving the presence signal;
    timestamping and storing the body scan in a vehicle memory;
    determining a set of body scan parameters from the body scan of the vehicle seat occupant, wherein the set of body scan parameters includes apparent weight, height, body mass index (BMI), and waist thickness;
    recording a sensor signature of the vehicle seat occupant;
    identifying the vehicle seat occupant by matching the sensor signature to a set sensor signatures of registered vehicle seat occupants stored in the vehicle memory;
    measuring a current body weight of the vehicle seat occupant;
    timestamping and storing the current body weight in the vehicle memory;
    determining changes between the current body weight and at least one stored body weight of the vehicle seat occupant having a timestamp recorded during an earlier time period;
    accessing GPS records regarding venues visited by the vehicle seat occupant during the earlier time period;
    associating each of the venues with a level of caloric intake based on a type of the venue, wherein the venues include restaurants, fast food restaurants, fitness centers, and grocery stores;
    generating a weight analysis by (i) correlating the weight changes of the vehicle seat occupant with the level of the caloric intake associated with the venues visited by the vehicle seat occupant, and (ii) correlating the weight changes, the set of body scan parameters and the GPS records of venues visited with weight information stored in the vehicle memory;

generating a weight management recommendation from the weight analysis;

notifying the vehicle seat occupant of the weight management recommendation;

updating the vehicle memory with the weight management recommendation; and transmitting the body weight changes and the body scan parameters to a data lake.

2. The method of claim 1, further comprising:

determining changes between the current body weight and at least one stored body weight of the vehicle seat occupant having a timestamp recorded during an earlier time period selected from at least one of:
  greater than two weeks and less than five years before the current body weight;
  greater than one month and less than three months before the current body weight; and
  greater than six months and less than one year before the current body weight.

3. The method of claim 1, further comprising:

comparing the current body weight with each body weight from an earlier time period until one of a change is detected and all body weights having earlier timestamps have been compared to the current body weight.

4. The method of claim 1, further comprising:

recording the sensor signature by at least one of an internal vehicle camera, an audio sensor, a fingerprint sensor, and a retinal sensor.

5. The method of claim 1, further comprising:

registering the vehicle with a weight management application by creating public and private pair keys in a vehicle computing system of the vehicle;

transmitting the public key to the weight management application;

creating a user profile for each vehicle seat occupant including at least a facial image, an age, a height, a weight, a gender, an ethnic group, an address, a credit card number and medical diseases of the vehicle seat occupant; and providing lists of preferred medical practitioners, dieticians, weight management centers, fitness centers and scalp care professionals and retail outlets of each vehicle seat occupant.

6. The method of claim 5, further comprising:

combining the vehicle seat occupant identification, the body weight changes, the set of body scan parameters and the GPS records of venues visited into a data packet;

transmitting the data packet to the weight management application.

7. The method of claim 6, further comprising:

receiving, by the weight management application, the data packet;

requesting, by the weight management application, a search related to the vehicle seat occupant body weight changes, the set of body scan parameters and the GPS records of venues visited;

receiving the request by a weight data artificial intelligence (AI) analytics circuitry module;

querying the data lake for information relating to the vehicle seat occupant body weight changes, the set of body scan parameters and the GPS records of venues visited;

searching, by the data lake, unstructured data and structured databases for matches to the query;

receiving, by the weight data AI analytics circuitry module, the matches to the query;

analyzing, by the weight data AI analytics circuitry module, the matches to determine weight conditions, treatment options for the weight conditions and at least one of weight loss or weight gain product information related to the weight conditions;

generating, by the weight data AI analytics circuitry module, a weight report;

providing the weight report to the weight management application for correlation with the vehicle seat occupant user profile;

generating a weight management recommendation;

transmitting the weight management recommendation to the vehicle;

updating the vehicle memory; and delivering the weight management recommendation to the vehicle seat occupant.

8. The method of claim 6, further comprising:

registering a smart device of the vehicle seat occupant with the weight management application by:

creating public and private pair keys with a smart device of the vehicle seat occupant;

transmitting the public key to the weight management application;

creating a vehicle seat occupant user profile including at least a facial image, an age, a height, a weight, a gender, an ethnic group, an address, a credit card number and previous weight and medical diseases of the vehicle seat occupant; and providing a list of preferred weight management professionals, dieticians, weight management centers, fitness centers and retail outlets.

9. The method of claim 8, further comprising:

receiving, by the weight management application, the data packet;

requesting, by the weight management application, a search related to the vehicle seat occupant weight information record;

receiving the request by a weight data artificial intelligence (AI) analytics circuitry module;

querying the data lake for information relating to the vehicle seat occupant body weight changes, the set of body scan parameters and the GPS records of venues visited;

searching, by the data lake, unstructured data and structured databases for matches to the query;

receiving, by the weight data AI analytics circuitry module, the matches to the query;

analyzing, by the weight data AI analytics circuitry module, the matches to determine weight conditions, treatment options for the weight conditions and at least one of weight loss or weight gain product information related to the weight conditions;

generating, by the weight data AI analytics circuitry module, a weight report;

providing the weight report to the weight management application for correlation with the vehicle seat occupant user profile;

generating a weight management recommendation;

transmitting the weight management recommendation to the smart device of the registered vehicle seat occupant.

10. The method of claim 7, wherein the weight management recommendation comprises at least one of:
- recommending a medical practitioner based on a home location or a current location of the vehicle seat occupant;
- recommending a weight management professional based on a home location or a current location of the vehicle seat occupant;
- recommending a dietician based on a home location or a current location of the vehicle seat occupant;
- recommending a weight management center based on a home location or a current location of the vehicle seat occupant;
- recommending a fitness center based on a home location or a current location of the vehicle seat occupant;
- recommending a fitness trainer based on a home location or a current location of the vehicle seat occupant;
- recommending weight management products;
- recommending retail websites of weight management products;
- recommending retail outlets for weight management products based on a home location or a current location of the vehicle seat occupant;
- recommending an exercise program;
- recommending low calorie restaurants based on a home location or current location of the vehicle seat occupant and the restaurant visit frequency record; and
- recommending a weight management regime.

11. A system for managing a weight of a vehicle seat occupant, comprising:
- a plurality of vehicles, each vehicle including:
  - at least one presence detector external to the vehicle configured for detecting the approach of a vehicle seat occupant and generating a presence signal;
  - at least one 360 degree camera external to the vehicle configured for performing a body scan of the vehicle seat occupant upon receiving the presence signal;
  - an image processor configured for receiving and time-stamping the body scan;
  - a body scan analysis circuitry module configured for determining a set of body scan parameters from the body scan, wherein the set of body scan parameters includes apparent weight, height, body mass index (BMI), and waist thickness;
  - at least one internal vehicle sensor configured for recording a sensor signature of the vehicle seat occupant, wherein the internal vehicle sensor is at least one of a plurality of cameras, an audio sensor, a fingerprint sensor and a retinal sensor;
  - at least one vehicle seat weight sensor configured for measuring a current body weight of the vehicle seat occupant;
  - a weight processor configured to receive the current body weight and timestamp the body weight;
  - a memory including a first database configured for storing, for each vehicle seat occupant, a user profile, at least one sensor signature, timestamped body scans, timestamped weight measurements and a second database configured for storing information related to weight management;
  - an identity circuitry module configured for identifying the vehicle seat occupant by matching the sensor signature to a sensor signature stored in the first database;
  - a weight comparison circuitry module configured for determining changes between the current body weight and at least one stored body weight of the vehicle seat occupant having a timestamp recorded during an earlier time period;
  - a GPS unit configured for generating trip information regarding venues visited by the vehicle seat occupant;
  - a central processing unit (CPU) operatively connected to the GPS unit and configured for accessing GPS trip information regarding venues visited by the vehicle seat occupant during the earlier time period;
  - a weight analysis circuitry module configured for associating each of the venues with a level of caloric intake based on a type of the venue, wherein the venues include restaurants, fast food restaurants, fitness centers, and grocery stores, and for generating a weight management recommendation by (i) correlating the weight changes of the vehicle seat occupant with the level of the caloric intake associated with the venues visited by the vehicle seat occupant, and (ii) correlating the set of body scan parameters, the weight changes and the trip information of venues visited during the earlier time period with the information related to weight management;
  - a user interface configured for delivering the weight management recommendation to the vehicle seat occupant;
  - wherein the CPU is further operatively connected to the at least one presence detector, the at least one 360 degree camera, the at least one vehicle seat weight sensor, the at least one internal vehicle sensor, the vehicle memory, the body scan analysis circuitry module, the image processor, the weight processor, the weight comparison circuitry module, the weight analysis circuitry module, the identity circuitry module and an onboard communications circuitry module;
  - wherein the onboard communications circuitry module is configured for transmitting a first data packet including the set of body scan parameters, the weight changes, the vehicle seat occupant identity and the GPS trip information regarding venues visited and for transmitting a second data packet including the set of body scan parameters, the weight changes, a set of anonymized information of the user profile and the GPS trip information regarding venues visited to a data lake.

12. A system of claim 11, comprising:
- wherein the at least one internal vehicle sensor includes a plurality of interior cameras, each camera having a field of view focused at the level of a face of a vehicle seat occupant, each camera configured to record a facial record of the vehicle seat occupant.

13. The system of claim 11, further comprising:
- a weight management application located in a data center, the weight management application including:
  - a registration circuitry module configured for registering each vehicle of the plurality of vehicles with the weight management application;
  - a transceiver configured for receiving the first data packet from the onboard communications circuitry module of each vehicle;
  - a weight analysis processor configured for requesting a search related to the body weight changes, the set of body scan parameters and the GPS records of venues visited of each vehicle seat occupant;
  - wherein the data center includes:
    - a weight data artificial intelligence (AI) analytics circuitry module configured to receive the request and generate search queries related to the body weight changes, the set of body scan parameters and the GPS records of venues visited of each vehicle seat occupant;

wherein the data lake is configured to receive the search queries and conduct the search of unstructured data and structured databases for matches to the queries;

wherein the weight data AI analytics circuitry module is further configured to analyze the matches to determine weight conditions, treatment options for the weight conditions and at least one of weight loss or weight gain product information related to the weight conditions and to generate a weight report;

wherein the weight analysis processor is further configured to correlate the weight report with the vehicle seat occupant user profile;

a weight management recommendation circuitry module configured to generate a vehicle seat occupant weight management recommendation;

wherein the transceiver is further configured to transmit the vehicle seat occupant weight management recommendation to the onboard communications circuitry module of the vehicle occupied by the vehicle seat occupant.

14. The system of claim 13, wherein the weight management recommendation comprises a recommendation to at least one of:
a medical practitioner based on a home location or a current location of the vehicle seat occupant;
a weight management professional based on a home location or a current location of the vehicle seat occupant;
a dietician based on a home location or a current location of the vehicle seat occupant;
a weight management center based on a home location or a current location of the vehicle seat occupant;
a fitness center based on a home location or a current location of the vehicle seat occupant;
weight management products;
retail websites for obtaining weight management products;
retail outlets for obtaining weight management products based on a home location or a current location of the vehicle seat occupant;
an exercise program;
low calorie restaurants based on a home location or current location of the vehicle seat occupant and the restaurant visit frequency record; and
a weight management regime.

15. The system of claim 13, the weight management application further comprises:
an application memory including:
a first database of subscriber information, the subscriber information including a user profile of each vehicle seat occupant of each of the plurality of vehicles;
a second database of sponsored content, wherein the sponsored content includes lists of medical practitioners, weight management professionals, dieticians, fitness centers, fitness trainers, weight management products, retail websites or retail outlets for purchasing weight management products and restaurants in the home location or current location of the vehicle seat occupant; and
wherein the registration circuitry module is further configured to register sponsors of weight related treatment or products.

16. The system of claim 15, comprising:
wherein the registration circuitry module is further configured to register a smart device of a vehicle seat occupant travelling in any of the plurality of vehicles with the weight management application, wherein registering the smart device includes:
receiving a public key from the smart device;
requesting profile information from the vehicle occupant including age, weight, gender, ethnic origins, previous weight and medical diseases of the vehicle seat occupant;
requesting lists of preferred medical practitioners, weight management professionals, dieticians, weight management centers, fitness centers, fitness trainers, weight management products and retail outlets; and
storing the public key, personal information and lists in the application memory.

17. The system of claim 16, further comprising:
wherein the weight management application is further configured to:
receive a body scan and current weight of the registered vehicle seat occupant whenever the vehicle seat occupant travels in any of the plurality of vehicles registered with the weight management application;
perform an analysis of the body scan and detect body scan parameters;
detect changes between a current body weight and at least one body weight of the vehicle seat occupant stored in the application memory having a timestamp recorded during an earlier time period;
access GPS trip information regarding venues visited by the vehicle seat occupant during the earlier time period;
request a search by the weight data AI analytics circuitry module of the data lake for information related to the body weight changes and the body scan of the registered vehicle seat occupant;
wherein the weight data AI analytics circuitry module is further configured to receive the request and generate search queries related to the body weight changes, the set of body scan parameters and the GPS records of venues visited of the registered vehicle seat occupant;
wherein the data lake is configured to receive the search queries and conduct the search of unstructured data and structured databases for matches to the queries;
wherein the weight data AI analytics circuitry module is further configured to analyze the matches to determine weight conditions, treatment options for the weight conditions and at least one of weight loss or weight gain product information related to the weight conditions and to generate a weight report;
wherein the weight analysis processor is further configured to correlate the weight report with the vehicle seat occupant user profile;
wherein the weight management recommendation circuitry module is further configured to generate a weight management recommendation for the registered vehicle seat occupant; and
wherein the transceiver is further configured to transmit the weight management recommendation to the smart device of the registered vehicle seat occupant.

18. The system of claim 17, wherein the weight management application is further configured to store the body weight, sets of body scan parameters and weight management recommendations of each of the identified vehicle seat occupants of each of the plurality of vehicles as unstructured data.

19. A non-transitory computer readable medium having instructions stored therein that, when executed by one or more processor, cause the one or more processors to perform a method for managing a weight of a vehicle seat occupant using vehicle cameras and vehicle weight data sensors, comprising:
- detecting an approach of the vehicle seat occupant to the vehicle and generating a presence signal;
- performing a body scan of the vehicle seat occupant upon receiving the presence signal;
- timestamping and storing the body scan in a vehicle memory;
- determining a set of body scan parameters from the body scan of the vehicle seat occupant, wherein the set of body scan parameters includes apparent weight, height, body mass index (BMI), and waist thickness;
- recording a sensor signature of the vehicle seat occupant;
- identifying the vehicle seat occupant by matching the sensor signature to a set sensor signatures of registered vehicle seat occupants stored in the vehicle memory;
- measuring a current body weight of the vehicle seat occupant;
- timestamping and storing the current body weight in the vehicle memory;
- determining changes between the current body weight and at least one stored body weight of the vehicle seat occupant having a timestamp recorded during an earlier time period;
- accessing GPS records regarding venues visited by the vehicle seat occupant during the earlier time period;
- associating each of the venues with a level of caloric intake based on a type of the venue, wherein the venues include restaurants, fast food restaurants, fitness centers, and grocery stores;
- generating a weight analysis by (i) correlating the weight changes of the vehicle seat occupant with the level of the caloric intake associated with the venues visited by the vehicle seat occupant, and (ii) correlating the weight changes, the set of body scan parameters and the GPS records of venues visited with weight information stored in the vehicle memory;
- generating a weight management recommendation from the weight analysis;
- notifying the vehicle seat occupant of the weight management recommendation;
- updating the vehicle memory with the weight management recommendation; and
- transmitting the body weight changes and the body scan parameters to a data lake.

20. The non-transitory computer readable medium method of claim 19, further comprising:
- registering the vehicle with a weight management application by creating public and private pair keys in a vehicle computing system of the vehicle;
- transmitting the public key to the weight management application;
- creating a user profile for each vehicle seat occupant including at least a facial image, an age, a height, a weight, a gender, an ethnic group, an address, a credit card number and medical diseases of the vehicle seat occupant;
- providing lists of preferred medical practitioners, dieticians, weight management centers, fitness centers and scalp care professionals and retail outlets of each vehicle seat occupant;
- combining the vehicle seat occupant identification, the body weight changes, the set of body scan parameters and the GPS records of venues visited into a data packet;
- transmitting the data packet to the weight management application;
- receiving, by the weight management application, the data packet;
- requesting, by the weight management application, a search related to the vehicle seat occupant body weight changes, the set of body scan parameters and the GPS records of venues visited;
- receiving the request by a weight data artificial intelligence (AI) analytics circuitry module;
- querying a data lake for information relating to the vehicle seat occupant body weight changes, the set of body scan parameters and the GPS records of venues visited;
- searching, by the data lake, unstructured data and structured databases for matches to the query;
- receiving, by the weight data AI analytics circuitry module, the matches to the query;
- analyzing, by the weight data AI analytics circuitry module, the matches to determine weight conditions, treatment options for the weight conditions and at least one of weight loss or weight gain product information related to the weight conditions;
- generating, by the weight data AI analytics circuitry module, a weight report;
- providing the weight report to the weight management application for correlation with the vehicle seat occupant user profile;
- generating a weight management recommendation;
- transmitting the weight management recommendation to the vehicle;
- updating the vehicle memory; and
- delivering the weight management recommendation to the vehicle seat occupant.

21. The method of claim 1, wherein the weight management recommendation includes a numerical value of the weight changes of the vehicle seat occupant, an identification of the venues visited by the vehicle seat occupant and the level of caloric intake of each of the visited venues, and a recommendation on whether to increase or decrease visits by the vehicle seat occupant to respective ones of the visited venues.

* * * * *